United States Patent
Bartolomé-Nebreda et al.

(10) Patent No.: US 8,895,562 B2
(45) Date of Patent: Nov. 25, 2014

(54) PIPERAZIN-1-YL-TRIFLUOROMETHYL-SUBSTITUTED-PYRIDINES AS FAST DISSOCIATING DOPAMINE 2 RECEPTOR ANTAGONISTS

(75) Inventors: José Manuel Bartolomé-Nebreda, Toledo (ES); Gregor James MacDonald, Zoersel (BE); Michiel Luc Maria Van Gool, Madrid (ES)

(73) Assignee: Janssen Pharmaceutica NV, Beerse (BE)

( * ) Notice: Subject to any disclaimer, the term of this patent is extended or adjusted under 35 U.S.C. 154(b) by 327 days.

(21) Appl. No.: 13/056,287

(22) PCT Filed: Jul. 29, 2009

(86) PCT No.: PCT/EP2009/059788
§ 371 (c)(1),
(2), (4) Date: Jan. 27, 2011

(87) PCT Pub. No.: WO2010/012758
PCT Pub. Date: Feb. 4, 2010

(65) Prior Publication Data
US 2011/0130408 A1  Jun. 2, 2011

(30) Foreign Application Priority Data
Jul. 31, 2008 (EP) .................................. 08161576

(51) Int. Cl.
*C07D 213/74* (2006.01)
*C07D 213/84* (2006.01)
*C07D 401/04* (2006.01)
*C07D 409/04* (2006.01)

(52) U.S. Cl.
CPC ............ *C07D 213/74* (2013.01); *C07D 213/84* (2013.01)
USPC ............ 514/253.01; 514/253.11; 514/253.12; 544/360; 544/364

(58) Field of Classification Search
None
See application file for complete search history.

(56) References Cited

U.S. PATENT DOCUMENTS

| | | | |
|---|---|---|---|
| 3,933,823 A | 1/1976 | Denzel et al. | |
| 3,933,832 A | 1/1976 | Langbein et al. | |
| 4,126,689 A | 11/1978 | Sanczuk et al. | |
| 4,197,304 A | 4/1980 | Hermans et al. | |
| 4,585,471 A | 4/1986 | Forster et al. | |
| 5,461,053 A | 10/1995 | Boigegrain et al. | |
| 5,560,931 A | 10/1996 | Eickhoff et al. | |
| 5,736,545 A | 4/1998 | Gadwood et al. | |
| 5,866,589 A | 2/1999 | Romero et al. | |
| 5,958,923 A | 9/1999 | Hellendahl et al. | |
| 7,335,658 B2 | 2/2008 | Chakka et al. | |
| 7,754,774 B2 | 7/2010 | Kobayashi et al. | |
| 8,058,243 B2 | 11/2011 | Tyers et al. | |
| 2007/0081953 A1 | 4/2007 | Dahms | |
| 2008/0227791 A1 | 9/2008 | Debruyn et al. | |
| 2010/0063058 A1 | 3/2010 | MacDonald et al. | |
| 2010/0069394 A1 | 3/2010 | MacDonald et al. | |
| 2010/0076187 A1 | 3/2010 | MacDonald et al. | |
| 2010/0092505 A1 | 4/2010 | Bianchi et al. | |
| 2010/0120860 A1 | 5/2010 | MacDonald et al. | |
| 2010/0137368 A1 | 6/2010 | MacDonald et al. | |
| 2010/0210687 A1 | 8/2010 | Cooper et al. | |
| 2011/0092505 A1* | 4/2011 | Burgis et al. ................ | 514/235.5 |
| 2011/0112107 A1 | 5/2011 | Bartolomé-Nebreda | |

FOREIGN PATENT DOCUMENTS

| | | |
|---|---|---|
| CA | 2009501 | 8/1990 |
| EP | 0211457 | 2/1987 |
| EP | 281309 | 9/1988 |
| EP | 532178 | 3/1993 |
| EP | 1443046 | 8/2004 |
| EP | 1621538 | 2/2006 |
| EP | 1506185 | 5/2006 |
| GB | 1539473 | 1/1979 |
| WO | WO 95/18118 | 7/1995 |
| WO | WO 96/02249 | 2/1996 |
| WO | WO 96/18628 | 6/1996 |
| WO | WO 96/35666 | 11/1996 |
| WO | WO 97/43279 | 11/1997 |
| WO | WO 99/09025 | 2/1999 |
| WO | WO 99/36407 | 7/1999 |
| WO | WO 01/98273 | 12/2001 |
| WO | WO 02/068409 | 9/2002 |
| WO | WO 03/045353 | 6/2003 |
| WO | WO 03/049736 | 6/2003 |

(Continued)

OTHER PUBLICATIONS

Garzya et al. Bioorganic & Medicinal Chemistry Letters, vol. 17, pp. 400-405 (2007).*

(Continued)

*Primary Examiner* — Emily Bernhardt
(74) *Attorney, Agent, or Firm* — Hal B. Woodrow

(57) ABSTRACT

The present invention relates to piperazin-1-yl-trifluoromethyl-substituted-pyridines that are fast dissociating dopamine 2 receptor antagonists, processes for preparing these compounds, pharmaceutical compositions comprising these compounds as an active ingredient. The compounds find utility as medicines for treating or preventing central nervous system disorders, for example schizophrenia, by exerting an antipsychotic effect without motor side effects.

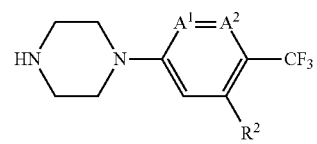

5 Claims, No Drawings

(56) References Cited

FOREIGN PATENT DOCUMENTS

| WO | WO 03/062215 | 7/2003 |
|---|---|---|
| WO | WO 03/066604 | 8/2003 |
| WO | WO 03/072548 | 9/2003 |
| WO | WO 2004/058729 | 7/2004 |
| WO | WO 2004/085406 | 10/2004 |
| WO | WO 2004/098555 | 11/2004 |
| WO | WO 2005/005779 | 1/2005 |
| WO | WO 2005/009976 | 2/2005 |
| WO | WO 2005/011655 | 2/2005 |
| WO | WO 2005/046581 | 5/2005 |
| WO | WO 2005/077914 | 8/2005 |
| WO | WO 2005/090317 | 9/2005 |
| WO | WO 2005/013907 | 11/2005 |
| WO | WO 2005/105779 | 11/2005 |
| WO | WO 2005/117883 | 12/2005 |
| WO | WO 2005/123692 | 12/2005 |
| WO | WO 2005/123693 | 12/2005 |
| WO | WO 2006/034440 | 3/2006 |
| WO | WO 2006055187 | 5/2006 |
| WO | WO 2007/001975 | 1/2007 |
| WO | WO 2007/048779 | 5/2007 |
| WO | WO 2007/130383 | 11/2007 |
| WO | WO 2008/019967 | 2/2008 |
| WO | WO 2008/068507 | 6/2008 |
| WO | WO 2008/098892 | 8/2008 |
| WO | WO 2010/012758 | 2/2010 |

OTHER PUBLICATIONS

Liu et al. Drug Development Research, vol. 70, pp. 145-168 (2009).*
International Search Report for PCT/EP2009/059788 dated Oct. 9, 2009.
Written Opinion for PCT/EP2009/059788 dated Oct. 9, 2009.
Joyce et al., Drug Discovery Today, vol. 10, No. 13, Jul. 2005, pp. 917-925.
Kapur et al., Am J Psychiatry, 2001; 158:3, pp. 360-369.
Leysen et al., Journal of Receptor Research, 4(7), 817-845 (1984).
Mitchell et al., Pharmacology & Therapeutics 108 (2005), 320-333.
Tao et al., Tetrahedron Letters 44 (2003) 7993-7996.
Abbott, A., Nature, vol. 447, May 24, 2007, p. 368-370.
Arlt, M. et al., Bioorganic & Medicinal Chemistry Letters; vol. 8; No. 15; p. 2033-2038, 1998.
Bartoszyk et al., "Anxiolytic Effects of Dopamine Receptor Ligands: I. Involvement of Dopamine Autoreceptors" Life Sciences, Pergamon Press, Oxford, GB, vol. 62, No. 7, Jan. 1, 1998, pp. 649-663.
Benjamin, et al., Biochemical Pharmacology; vol. 72; No. 6; p. 770-782, 2006.
Bianchi "Current Issues in CNS drug" p. 1-3 (2011).
Binggeli et al., CA148:285064 (2008), (7pages).
Braga et al., Roy. Soc. Chem. Chem. Commun. p. 3635-3645 (2005).
Cell Surface Receptor, Wikipedia, p. 1-6 (2012).
Chabner et al., Chemotherapy of Neoplastic Diseases, Neoplastic Agents in, Goodman & Gilman's: The Pharmacological Basis of Therapeutics 1315-1403, 1315 (L.L. Brunton et al., eds., 11th ed., 2006).
Contreras, Jean Marie, "Aminopyridazines as Acetylcholinesterase Inhibitors", J. Med. Chem. (1999),42 (4), 730-741.
Cook et al., CA132_347492 (2000), (3 pages).
Dean et al., J. Org. Chem. 1993, 58, 7916-7917.
Eichenberger, K.; Rometsch, R..; Druey, J. Australian Journal of Chemistry 1956, 9, 1755-1764. See English abstract provided.
Fryatt et al., J. Bioorganic and Medicinal Chemistry, 2004, 12, 1667-1687.
Genin et al., "Synthesis and structure-activity relationships of the (alkylamino)piperidine-containing BHAP class of non-nucleoside reverse transcriptase inhibitors: effect of 3-alkylpyridine ring substitution" J. Med. Chem., vol. 42, No. 20, 1999, pp. 4140-4149.
Genin et al., "Synthesis and bioactivity of novel bis(heteroaryl)piperazine (BHAP) reverse transcriptase inhibitors: structure-activity relationships and increased metabolic stabilita of novel substituted pyri di ne' analogs" J. Med. Chem., vol. 39, No. 26, 1996, pp. 5267-5275.
Gillaspy et al., Tetrahedron Letters 1995, 36, 7399-7402.
Goodman et al., Tetrahedron 1999, 55, 15067-15070.
Griesser, in Chapter 8, The Importance of Solvates (pp. 211-230), in the text, Polymorphism: In the Pharmaceutical Industry, Hilfiker, 2006.
Grundt et al., Bioorg. Med. Chem. Lett 17(3) 745-749 (2007).
Holenz et al., Drug discovery today; vol. 11; No. 7-8; p. 283-299, 2006.
Kapitulnik, J., Frontiers in Pharm. p. 1-2, (2011).
Kikuchi et al., J. Med. Chem. (1999), 42 (4), 730-741.
Kortagere et al., "Certain 1,4-disubstituted aromati c piperidines and piperazines with extreme selectivity for the Dopamine D4 receptor interact with a common receptor microdomain" Molecular Pharmacology, vol. 66, No. 6, 2004, pp. 1491-1499.
Kula et al., "Neuropharmacological assessment of potential dopamine D4 receptor-selective radioligands" European Journal of Pharmacology, Amsterdam, NL, vol. 367, Jan. 1, 1999, pp. 139-142.
Kula et al., "RBI-257: A highly potent dopamine D receptor-selective ligand", European Journal of Pharmacology, 331 (1997), pp. 333-336.
Kula et al., CA127:171455 (1997), Abstract version, (1 page).
Lovenberg et al., Cloning of rat histamine H3 receptor reveals distinct species pharmacological profiles. J Pharmacol Expt Ther 2000;293:771-778.
Moragues, J. et al., "Dopaminergic Activity in a series of n-substituted 2-aminopyrimidines" Farmaco, vol. 35, No. 11, 1980, pp. 951-964.
Munson et al., "Synthesis of 2-AlkYlamino-3-fluoropyridines Using Buchwald Conditions" Synthetic Communications, Taylor & Francis, Philadelphia, PA, vol. 34, No. 5, Jan. 1, 2004, pp. 759-766.
Okuyama et al., Life Sci. 65(20) 2109-2125 (1999).
Phedias et al., CA148:509885 (2008), (1 page).
Poupaert, J.H., Drug Design: Basic Principles and Applications, in 2 Encyclopedia of Pharmaceutical Technology 1362-1369, 1367 (James Swarbrick ed., 3rd ed., 2007).
Rodefer et al., Neuropsychopharmacology (2008) 2657-2666.
Schlachter et al. "Substituted 4-aminopiperidines having high in vitro affinity and selectivity for the cloned human dopami ne D4 receptor" European Journal of Pharmacology, vol. 322, 1997, pp. 283-286.
Seddon, K., Crystal. Growth & Design 4(6)1087 (2004).
TenBrink, CA124:8845 (1995), (1 page).
Vippagunta et al., "Crystalline solids", Adv. Drug Delivery Reviews 48 (2001) 3-26.
Wood et al., Exp. Opin. Invest. Drugs 1696)771-775 (2007).
Xiao et al., Bioorg, Med. Chem. Lett. v.21, p. 861-864 (2011).
Yamada et al., Involvement of Septal and Striatal Dopamine D-2 Receptors in Yawning Behavior in Rats, Psychopharmacology, vol. 1, 1986, pp. 9-13.
Zablotskaya et al., Chem. Het. Compo v.38 (7), p. 859-866 (2002).
Zhang et al., Exp. Opin. Ther. Patents 16(5) 587-630 (2006).
Goodman and Gilman's The Pharmacologic Basis of Therapeutics, 12th Edition, Chapter 16, "Pharmacotherapy of Psychosis and Mania" by Jonathan M. Meyer, pp. 417-455, 2011.
Fisas et al., British Journal of Pharmacology. 2006, 148: 973-983.
Hannon et al., Acta Biologica Szegediensis. 2002, 46(1-2): 1-12.

* cited by examiner

PIPERAZIN-1-YL-TRIFLUOROMETHYL-SUBSTITUTED-PYRIDINES AS FAST DISSOCIATING DOPAMINE 2 RECEPTOR ANTAGONISTS

CROSS REFERENCE TO RELATED APPLICATIONS

This application claims priority from and is the national stage of PCT Application No. PCT/EP2009/059788, filed Jul. 29, 2009, which claims priority from European Patent Application No. 08161576.7, filed Jul. 31, 2008, the entire disclosures of which are hereby incorporated in their entirety.

FIELD OF THE INVENTION

The present invention relates to piperazin-1-yl-trifluoromethyl-substituted-pyridines that are fast dissociating dopamine 2 receptor antagonists, processes for preparing these compounds, and pharmaceutical compositions comprising these compounds as an active ingredient. The compounds find utility as medicines for treating or preventing central nervous system disorders, for example schizophrenia, by exerting an antipsychotic effect without motor side effects.

DESCRIPTION OF THE INVENTION

Schizophrenia is a severe and chronic mental illness that affects approximately 1% of the population. Clinical symptoms are apparent relatively early in life, generally emerging during adolescence or early adulthood. The symptoms of schizophrenia are usually divided into those described as positive, including hallucinations, delusions and disorganized thoughts and those referred to as negative, which include social withdrawal, diminished affect, poverty of speech and the inability to experience pleasure. In addition, schizophrenic patients are suffering from cognitive deficits, such as impaired attention and memory. The etiology of the disease is still unknown, but aberrant neurotransmitter actions have been hypothesized to underlie the symptoms of schizophrenia. The dopaminergic hypothesis is one most often considered; it proposes that hyperactivity of dopamine transmission is responsible for the positive symptoms observed in schizophrenic patients. This hypothesis is based on the observation that dopamine enhancing drugs, such as amphetamine or cocaine, may induce psychosis, and on the correlation that exists between clinical doses of antipsychotics and their potency in blocking dopamine D2 receptors. All marketed antipsychotics mediate their therapeutic efficacy against positive symptoms by blocking the dopamine D2 receptor. Apart from the clinical efficacy, it appears that the major side effects of antipsychotics, such as extrapyramidal symptoms (EPS) and tardive dyskinesia, are also related to dopamine antagonism. Those debilitating side effects appear most frequently with the typical or first generation of antipsychotics (e.g., haloperidol). They are less pronounced with the atypical or second generation of antipsychotics (e.g., risperidone, olanzapine) and even virtually absent with clozapine, which is considered the prototypical atypical antipsychotic. Among the different theories proposed for explaining the lower incidence of EPS observed with atypical antipsychotics, the one that has caught a lot of attention during the last fifteen years, is the multireceptor hypothesis. It follows from receptor binding studies showing that many atypical antipsychotics interact with various other neurotransmitter receptors in addition to dopamine D2 receptors, in particular with the serotonin 5-HT2 receptors, whereas typical antipsychotics like haloperidol bind more selectively to the D2 receptors. This theory has been challenged in recent years because all major atypical antipsychotics fully occupy the serotonin 5-HT2 receptors at clinically relevant dosages but still differ in inducing motor side-effects. As an alternative to the multireceptor hypothesis, Kapur and Seeman ("Does fast dissociation from the dopamine D2 receptor explain the action of atypical antipsychotics?: A new hypothesis", Am. J. Psychiatry 2001, 158:3 p. 360-369) have proposed that atypical antipsychotics can be distinguished from typical antipsychotics by the rates at which they dissociate from dopamine D2 receptors. The fast dissociation from the D2 receptor would make an antipsychotic more accommodating of physiological dopamine transmission, permitting an antipsychotic effect without motor side effects. This hypothesis is particularly convincing when one considers clozapine and quetiapine. These two drugs have the fastest rate of dissociation from dopamine D2 receptors and they carry the lowest risk of inducing EPS in humans. Conversely, typical antipsychotics associated with a high prevalence of EPS, are the slowest dissociating dopamine D2 receptor antagonists. Therefore, identifying new drugs based on their rate of dissociation from the D2 receptor appears a valid strategy to provide new atypical antipsychotics.

As stated previously, current atypical antipsychotics interact with many different neurotransmitter receptors. Some of these interactions (such as the blockade of serotonin 5-HT6 and dopamine D3 receptors) may be beneficial when cognitive impairment and negative symptoms are considered. Indeed, numerous preclinical data have shown that 5-HT6 receptor antagonism has positive effects on cognitive processes in rodents (Mitchell and Neumaier (2005) 5-HT6 receptors: a novel target for cognitive enhancement. Pharmacology & Therapeutics 108:320-333). 5-HT6 antagonism has also been linked to appetite and food intake suppression. Further, D3 receptor antagonism enhances social interaction in rats suggesting a possible benefit on negative symptoms in schizophrenic patients (Joyce and Millan (2005) Dopamine D3 receptor antagonist as therapeutic agents. Drug Discovery Today 10: 917-925). On the other hand, other interactions (such as with adrenergic α1, histamine H1 and serotonin 5-HT2C receptors) are implicated in mediating side-effects, including hypotension, sedation, metabolic disorders and weight gain. Therefore, an additional goal is to combine fast dissociating D2 receptor properties with inhibition of serotonin 5-HT6 and dopamine D3 receptors in the absence of interactions with adrenergic α1, histamine H1 and serotonin 5-HT2C receptors. Such a profile is expected to provide novel compounds efficacious against positive symptoms, negative symptoms and cognitive deficits while having less or none of the major side-effects associated with current antipsychotics.

It is the object of the present invention to provide novel compounds that are fast dissociating dopamine 2 receptor antagonists as well as serotonin 5-HT6 and dopamine D3 receptor antagonists which have an advantageous pharmacological profile as explained hereinbefore, in particular reduced motor side effects, and moderate or negligible interactions with other receptors resulting in reduced risk of developing metabolic disorders.

The present invention is concerned with a compound of Formula (I):

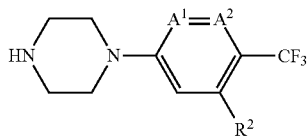

or a stereoisomeric form thereof, wherein
-A$^1$=A$^2$- is —N=CR$^1$— or —CR$^1$=N—;
R$^1$ is hydrogen, hydroxy, halo, cyano, C$_{1-3}$alkyloxy or C$_{1-3}$alkyl;
R$^2$ is phenyl; phenyl substituted with one, two or three substituents selected from the group consisting of halo, cyano, C$_{1-3}$alkyl, hydroxyC$_{1-3}$alkyl, mono- and polyhalo-C$_{1-3}$alkyl, C$_{1-3}$alkyloxy, C$_{1-3}$alkyloxyC$_{1-3}$alkyl, aminocarbonyl, mono- and di(C$_{1-3}$alkyl)aminocarbonyl, amino, mono- and di(C$_{1-3}$alkyl)amino; pyridinyl; pyridinyl substituted with one or two substituents selected from the group consisting of halo, C$_{1-3}$ alkyloxy, arylC$_{1-3}$alkyloxy, mono- and di(C$_{1-3}$alkyl)amino, and arylC$_{1-3}$alkylamino;
thienyl substituted with one or two substituents selected from the group consisting of halo and C$_{1-3}$alkyl;
or a solvate thereof or a salt thereof.

The compounds according to the invention are fast dissociating D$_2$ receptor antagonists. In addition, the present compounds have approximately the same affinity for dopamine D3 and serotonin 5-HT6 receptors as to dopamine D2 receptors. Insofar as tested, the compounds are antagonists at the three receptor subtypes. This property renders the compounds according to the invention especially suitable for use as a medicine in the treatment or prevention of schizophrenia, schizophreniform disorder, schizoaffective disorder, delusional disorder, brief psychotic disorder, shared psychotic disorder, psychotic disorder due to a general medical condition, substance-induced psychotic disorder, psychotic disorder not otherwise specified; psychosis associated with dementia; major depressive disorder, dysthymic disorder, premenstrual dysphoric disorder, depressive disorder not otherwise specified, bipolar I disorder, bipolar II disorder, cyclothymic disorder, bipolar disorder not otherwise specified, mood disorder due to a general medical condition, substance-induced mood disorder, mood disorder not otherwise specified; generalized anxiety disorder, obsessive-compulsive disorder, panic disorder, acute stress disorder, post-traumatic stress disorder, mental retardation, pervasive developmental disorders, attention deficit disorders, attention-deficit/hyperactivity disorder, disruptive behavior disorders, personality disorder of the paranoid type, personality disorder of the schizoid type, personality disorder of the schizotypical type, tic disorders, Tourette's syndrome, substance dependence; substance abuse; substance withdrawal; trichotillomania; and conditions wherein cognition is impaired, Alzheimer's disease, Parkinson's disease, Huntingdon's disease, Lewy Body Dementia, dementia due to HIV disease, dementia due to Creutzfeldt-Jakob disease; amnestic disorders; mild cognitive impairment; and age-related cognitive decline; and feeding disorders such as anorexia and bulimia; and obesity.

A skilled person can make a selection of compounds based on the experimental data provided in the Experimental Part hereinafter. Any selection of compounds is embraced within this invention.

The invention relates to compounds of Formula (I) and stereoisomeric forms thereof, wherein
-A$^1$=A$^2$- is —N=CR$^1$—;
R$^1$ is hydrogen, cyano or methoxy;
R$^2$ is phenyl or phenyl substituted with halo; and the solvates and the salts thereof.

The invention further relates to compounds of Formula (I) and stereoisomeric forms thereof, wherein
-A$^1$=A$^2$- is —CR$^1$=N—;
R$^1$ is hydrogen, methyl, cyano, hydroxy or methoxy;
R$^2$ is phenyl or phenyl substituted with halo; and the solvates and the salts thereof.

Amongst the compounds of Formula (I) and the stereoisomeric forms thereof, the most interesting are, for example,
5-Phenyl-3-piperazin-1-yl-6-trifluoromethyl-pyridin-2-ol (A17),
1-[4-(4-Fluoro-phenyl)-5-trifluoromethyl-pyridin-2-yl]-piperazine (B1),
4-Phenyl-6-piperazin-1-yl-3-trifluoromethyl-pyridine-2-carbonitrile (B2),
1-(6-Methoxy-4-phenyl-5-trifluoromethyl-pyridin-2-yl)-piperazine (B3),
1-(5-Phenyl-6-trifluoromethyl-pyridin-3-yl)-piperazine (B4),
1-(2-Methoxy-5-phenyl-6-trifluoromethyl-pyridin-3-yl)-piperazine (B5),
1-[5-(4-Fluoro-phenyl)-2-methoxy-6-trifluoromethyl-pyridin-3-yl]-piperazine (B6),
5-Phenyl-3-piperazin-1-yl-6-trifluoromethyl-pyridine-2-carbonitrile (B7) and
1-(2-Methyl-5-phenyl-6-trifluoromethyl-pyridin-3-yl)-piperazine (B8)
and the solvates and the salts thereof.

Throughout this application, the term "C$_{1-3}$alkyl" when used alone and when used in combinations such as "C$_{1-3}$alkyloxy", "diC$_{1-3}$alkylamino", includes, for example, methyl, ethyl, propyl, 1-methylethyl; the term halo includes fluoro, chloro, bromo, and iodo; the term "monohaloC$_{1-3}$alkyl" includes for example fluoromethyl, chloromethyl and 1-fluoroethyl; the term "polyhaloC$_{1-3}$alkyl" includes for example difluoromethyl, trifluoromethyl, 1,1,1-trifluoroethyl, pentafluoroethyl, heptafluoropropyl and nonafluorobutyl.

For therapeutic use, salts of the compounds of formula (I) are those wherein the counterion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not, are included within the ambit of the present invention.

The pharmaceutically acceptable salts are defined to comprise the therapeutically active non-toxic acid addition salts forms that the compounds according to Formula (I) are able to form. Said salts can be obtained by treating the base form of the compounds according to Formula (I) with appropriate acids, for example inorganic acids, for example hydrohalic acid, in particular hydrochloric acid, hydrobromic acid, sulfuric acid, nitric acid and phosphoric acid; organic acids, for example acetic acid, hydroxyacetic acid, propanoic acid, lactic acid, pyruvic acid, oxalic acid, malonic acid, succinic acid, maleic acid, mandelic acid, fumaric acid, malic acid, tartaric acid, citric acid, methanesulfonic acid, ethanesulfonic acid, benzenesulfonic acid, p-toluenesulfonic acid, cyclamic acid, salicylic acid, p-aminosalicylic acid, pamoic acid and mandelic acid. Conversely, said salts forms can be converted into the free forms by treatment with an appropriate base.

The term solvates refers to hydrates and alcoholates which the compounds of Formula (I) may form.

The term "stereochemically isomeric forms" as used hereinbefore defines all the possible isomeric forms that the compounds of Formula (I) may possess. Unless otherwise mentioned or indicated, the chemical designation of compounds denotes the mixture of all possible stereochemically isomeric forms, said mixtures containing all diastereomers and enantiomers of the basic molecular structure. More in particular, stereogenic centers may have the R—or S-configuration; substituents on bivalent cyclic (partially) saturated radicals may have either the cis—or trans-configuration. Compounds encompassing double bonds can have an E or Z-stereochemistry at said double bond. Stereochemically isomeric forms of the compounds of Formula (I) are embraced within the scope of this invention.

In the framework of this application, an element, in particular when mentioned in relation to a compound according to Formula (I), comprises all isotopes and isotopic mixtures of this element, either naturally occurring or synthetically produced, either with natural abundance or in an isotopically enriched form. Radiolabelled compounds of Formula (I) may comprise a radioactive isotope selected from the group of $^3$H, $^{11}$C, $^{18}$F, $^{122}$I, $^{123}$I, $^{125}$I, $^{131}$I, $^{75}$Br, $^{76}$Br, $^{77}$Br and $^{82}$Br. Preferably, the radioactive isotope is selected from the group of $^3$H, $^{11}$C and $^{18}$F.

The compounds of Formula (I) as prepared in the processes described below may be synthesized in the form of racemic mixtures of enantiomers that can be separated from one another following art-known resolution procedures. The racemic compounds of Formula (I) may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of Formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound would be synthesized by stereospecific methods of preparation. These methods will advantageously employ enantiomerically pure starting materials.

Preparation

Compounds of Formula (I) wherein -$A^1$=$A^2$- is —N=$CR^1$—, $R^1$ is hydrogen and $R^2$ is as defined before, can be prepared by reacting a compound of Formula (II)

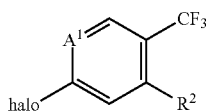

(II)

where $A^1$ is N, $R^2$ is as defined before and halo is chloro, bromo or iodo, with piperazine, in the presence of a suitable base, such as diisopropylethylamine, in a suitable solvent, such as acetonitrile, under suitable reaction conditions, such as a convenient temperature, either by conventional heating or under microwave irradiation for a period of time to ensure the completion of the reaction.

Compounds of Formula (II) wherein where $A^1$ is N, $R^2$ is as defined before and halo is chloro, bromo or iodo, can be prepared by reacting a compound of Formula (III)

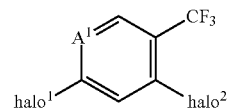

(III)

where $A^1$ is N, $R^2$ is as defined before and halo$^1$ and halo$^2$ are independently chloro, bromo or iodo, with an arylboronic acid in the presence of a suitable catalyst, such as tetrakis (triphenylphosphine)palladium (0), in the presence of suitable base, such as potassium phosphate, in a suitable inert solvent such as a mixture of 1,4-dioxane and water, under suitable reaction conditions, such as a convenient temperature, either by conventional heating or under microwave irradiation for a period of time to ensure the completion of the reaction.

Compounds of Formula (III) where $A^1$ is N, halo$^1$ is chloro and halo$^2$ is iodo, can be obtained commercially. Compounds of Formula (III) where $A^1$ is N and halo$^1$ and halo$^2$ are chloro, can be obtained by procedures similar to those described in Noble, S. A.; Oshiro, G.; Malecha, J. W.; Zhao, C.; Robinson, C. K. M.; Duron, S. G.; Sertic, M.; Lindstrom, A.; Shiau, Andrew; B., Christopher; K., Mehmet; L., Boliang; G., Steven. 2006, WO 2006055187 A1 20060526.

Compounds of Formula (I) wherein -$A^1$=$A^2$-, $R^2$ are as defined before, can also be prepared by deprotection of the protecting group in a compound of Formula (IV)

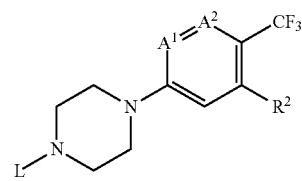

(IV)

where L represents a suitable protecting group, such as tert-butyloxycarbonyl, -$A^1$=$A^2$-$R^1$ and $R^2$ are as defined before, under suitable conditions, such as trifluoroacetic acid in dichloromethane or hydrochoric acid in 1,4-dioxane when L represents a tert-butyloxycarbonyl group.

Compounds of Formula (IV) wherein -$A^1$=$A^2$- is —N=$CR^1$—, $R^1$ is cyano and $R^2$ is as defined before and L represents a suitable protecting group, such as tert-butyloxycarbonyl, can be prepared by reacting a compound of Formula (IVa)

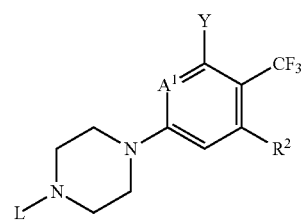

(IVa)

where $A^1$ is N, $R^2$ is as defined before, L represents a suitable protecting group, such as tert-butyloxycarbonyl, and Y represents halo, e.g. chloro, bromo or iodo, with zinc cyanide in the presence of a suitable catalyst, such as tetrakis(triphenylphosphine)palladium (0), in a suitable solvent, such as N,N-dimethylformamide under suitable reaction conditions, such as a convenient temperature, either by conventional heating or under microwave irradiation for a period of time to ensure the completion of the reaction.

Compounds of Formula (IVa) wherein $A^1$ is N and $R^2$ is as defined before and Y represents halo, e.g. chloro, bromo or iodo may be prepared by reacting a compound of Formula (V)

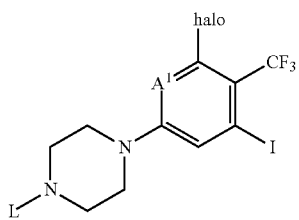

(V)

wherein $A^1$ is N, L represents a suitable protecting group, such as tert-butyloxycarbonyl, and halo is chloro, bromo or iodo with an arylboronic acid in the presence of a suitable catalyst, such as trans-Pd(OAc)$_2$(Cy$_2$NH)$_2$ (prepared by following the procedure described in Tao, B.; Boykin, D. W. Tetrahedron Lett. 2003, 44, 7993-7996), in the presence of suitable base, such as potassium phosphate, in a suitable inert solvent such as ethanol, under suitable reaction conditions, such as a convenient temperature, either by conventional heating or under microwave irradiation for a period of time to ensure the completion of the reaction.

Compounds of Formula (V) wherein $A^1$ is N, L represents a suitable protecting group, such as tert-butyloxycarbonyl, and halo is chloro, bromo or iodo, may be prepared by reacting a compound of Formula (VI)

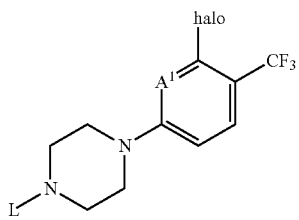

(VI)

wherein $A^1$ is N, L represents a suitable protecting group, such as tert-butyloxycarbonyl and halo is chloro, bromo or iodo, with iodine in the presence of a suitable base, such as a mixture of butyllithium and 2,2,6,6-tetramethylpiperidine, in a suitable inert solvent, such as tetrahydrofuran, at low temperatures, typically ranging from −78° C. to 0° C.

Compounds of Formula (VI) where $A^1$ is N, L represents a suitable protecting group, such as tert-butyloxycarbonyl, and halo is chloro or iodo, can be prepared by reacting a compound of Formula (VII)

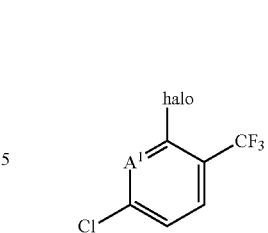

(VII)

wherein $A^1$ is N and halo is chloro, bromo or iodo, with a piperazine of Formula (VIII)

(VIII)

where L represents a suitable protecting group, such as tert-butyloxycarbonyl, in the presence of a suitable base, such as diisopropylethylamine, in a suitable solvent, such as acetonitrile, and under suitable reaction conditions, such as a convenient temperature, either by conventional heating or under microwave irradiation for a period of time to ensure the completion of the reaction.

Compounds of Formula (VII) where $A^1$ is N and halo is chloro, or iodo, can be obtained commercially.

Compounds of Formula (VIII) wherein L represents a suitable protecting group, such as tert-butyloxycarbonyl, can be obtained commercially.

Compounds of Formula (IV) wherein -$A^1$=$A^2$- is —N=CR$^1$—, $R^1$ is C$_{1-3}$alkyl, $R^2$ is as defined before and L represents a suitable protecting group, such as tert-butyloxycarbonyl, can be prepared by reacting a compound of Formula (IVa) where $A^1$ is N, $R^2$ is as defined before, L represents a suitable protecting group, such as tert-butyloxycarbonyl, and halo is chloro, bromo or iodo, with an alkyltin reagent in the presence of a suitable catalyst, such as bis(triphenylphosphine)palladium (II) dichloride, and in the presence of a suitable inorganic salt, such as lithium chloride, in a suitable solvent, such as N,N-dimethylformamide, under suitable reaction conditions, such as a convenient temperature, either by conventional heating or under microwave irradiation for a period of time to ensure the completion of the reaction.

Compounds of Formula (IV) wherein -$A^1$=$A^2$- is —N=CR$^1$—, $R^1$ is C$_{1-3}$alkyloxy, $R^2$ is as defined before and L represents a suitable protecting group, such as tert-butyloxycarbonyl, can be prepared by reacting a compound of Formula (IVa) where $A^1$ is N, $R^2$ is as defined before, L represents a suitable protecting group, such as tert-butyloxycarbonyl, and halo is chloro, bromo or iodo, with an alcohol in the presence of a suitable base, such as the sodium or potassium salt of the corresponding alcohol, in a suitable solvent, such as the corresponding alcohol, under suitable reaction conditions, such as a convenient temperature, either by conventional heating or under microwave irradiation for a period of time to ensure the completion of the reaction.

Compounds of Formula (IV) wherein -$A^1$=$A^2$- is —CR$^1$=N—, $R^1$ is hydrogen, $R^2$ is as defined before and L represents a suitable protecting group, such as tert-butyloxycarbonyl, can be prepared by reacting a compound of Formula (IX)

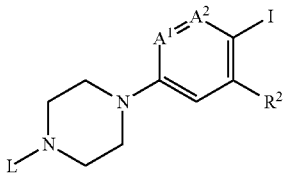

(IX)

where -$A^1$=$A^2$- is —$CR^1$=N—, $R^1$ is hydrogen, $R^2$ is as defined before and L represents a suitable protecting group, such as tert-butyloxycarbonyl, with methyl fluorosulfonyldifluoroacetate, in the presence of a suitable catalyst, such as copper (I) iodide, in a suitable solvent, such as N,N-dimethylformamide, under suitable reaction conditions, such as a convenient temperature, either by conventional heating or under microwave irradiation for a period of time to ensure the completion of the reaction.

Compounds of Formula (IX) wherein -$A^1$=$A^2$- is —$CR^1$=N—, $R^1$ is hydrogen, $R^2$ is as defined before and L represents a suitable protecting group, such as tert-butyloxycarbonyl, can be prepared by reacting a compound of Formula (X)

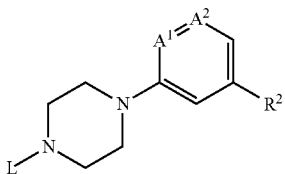

(X)

where -$A^1$=$A^2$- is —$CR^1$=N—, $R^1$ is hydrogen, $R^2$ is as defined before and L represents a suitable protecting group, such as tert-butyloxycarbonyl, with iodine in the presence of a suitable base, such as silver trifluoroacetate, in a suitable solvent, such as methanol, under suitable reaction conditions, such as a convenient temperature, typically ranging between room temperature and 100° C., either by conventional heating or under microwave irradiation for a period of time to ensure the completion of the reaction.

Compounds of Formula (X) wherein -$A^1$=$A^2$- is —$CR^1$=N—, $R^1$ is hydrogen, $R^2$ is as defined before and L represents a suitable protecting group, such as tert-butyloxycarbonyl, can be prepared by reacting a compound of Formula (XI)

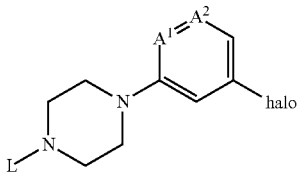

(XI)

where -$A^1$=$A^2$- is —$CR^1$=N—, $R^1$ is hydrogen, L represents a suitable protecting and halo is chloro, bromo or iodo with an arylboronic acid in the presence of a suitable catalyst, such as palladium 10% on activated charcoal, in the presence of a suitable ligand, such as dicyclohexylphosphino-2',4',6'-triisopropylbiphenyl, in the presence of suitable base, such as potassium carbonate, in a suitable inert solvent such as a mixture of N,N-dimethylacetamide and water, under suitable reaction conditions, such as a convenient temperature, either by conventional heating or under microwave irradiation for a period of time to ensure the completion of the reaction.

Compounds of Formula (XI) where -$A^1$=$A^2$- is —$CR^1$=N—, $R^1$ is hydrogen, L represents a suitable protecting and halo is chloro, bromo or iodo may be prepared by reacting an compound of Formula (XII)

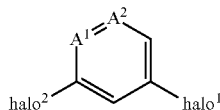

(XII)

where -$A^1$=$A^2$- is —$CR^1$=N—, $R^1$ is hydrogen and halo$^1$ and halo$^2$ are chloro, bromo or iodo with a piperazine of Formula (VIII) where L represents a suitable protecting group, such as tert-butyloxycarbonyl, in the presence of a suitable catalyst, such as tris(dibenzylideneacetone)dipalladium (0) chloroform adduct, in the presence of a suitable ligand, such as (R)-(+)-2,2'-bis(diphenylphosphino)-1,1'-binaphthyl, in the presence of a suitable base, such as sodium tert-butoxide, in a suitable solvent, such as toluene, and under suitable reaction conditions, such as a convenient temperature, either by conventional heating or under microwave irradiation for a period of time to ensure the completion of the reaction.

Compounds of Formula (XII) where -$A^1$=$A^2$- is —$CR^1$=N—, $R^1$ is hydrogen halo$^1$ and halo$^2$ are independently chloro, bromo or iodo, can be obtained commercially.

Compounds of Formula (IV) wherein -$A^1$=$A^2$- is —$CR^1$=N—, $R^1$ is $C_{1-3}$alkyloxy, $R^2$ is as defined before and L represents a suitable protecting group, such as tert-butyloxycarbonyl, can be prepared by reacting a compound of Formula (XIII)

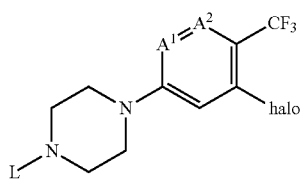

(XIII)

wherein -$A^1$=$A^2$- is —$CR^1$=N—, $R^1$ is $C_{1-3}$alkyloxy, L represents a suitable protecting group, such as tert-butyloxycarbonyl and halo is chloro, bromo or iodo, with an arylboronic acid in the presence of a suitable catalyst, such as palladium 10% on activated charcoal, in the presence of a suitable ligand, such as dicyclohexylphosphino-2',4',6'-triisopropylbiphenyl, in the presence of suitable base, such as potassium carbonate, in a suitable inert solvent such as a mixture of N,N-dimethylacetamide and water, under suitable reaction conditions, such as a convenient temperature, either by conventional heating or under microwave irradiation for a period of time to ensure the completion of the reaction.

Compounds of Formula (IV) where -$A^1$=$A^2$- is —$CR^1$=N—, $R^1$ is $C_{1-3}$alkyloxy, L represents a suitable protecting group, such as tert-butyloxycarbonyl and halo is chloro, bromo or iodo, can be prepared by reacting a compound of Formula (XIV)

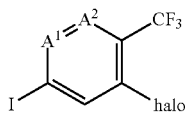

(XIV)

wherein -A$^1$=A$^2$- is —CR$^1$=N—, R$^1$ is C$_{1-3}$alkyloxy and halo is chloro, bromo or iodo, with a piperazine of Formula (VIII) where L represents a suitable protecting group, such as tert-butyloxycarbonyl, in the presence of a suitable catalyst, palladium (II) acetate, in the presence of a suitable ligand, such as (R)-(+)-2,2'-bis(diphenylphosphino)-1,1'-binaphthyl, in the presence of a suitable base, such as cesium carbonate, in a suitable solvent, such as toluene, and under suitable reaction conditions, such as a convenient temperature, either by conventional heating or under microwave irradiation for a period of time to ensure the completion of the reaction.

Compounds of Formula (XIV) wherein -A$^1$=A$^2$- is —CR$^1$=N—, R$^1$ is C$_{1-3}$alkyloxy and halo is chloro, bromo or iodo, may be prepared by reacting a compound of Formula (XV)

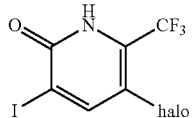

(XV)

wherein halo is chloro, bromo or iodo, with a reagent of Formula R$^3$—W wherein R$^3$ is C$_{1-3}$alkyl and W represents a leaving group such as halo, e.g. chloro, bromo or iodo, or a sulfonyloxy group, e.g. methylsulfonyloxy, trifluoromethylsulfonyloxy, or methylphenylsulfonyloxy in the presence of a base such as silver carbonate or diisopropylethylamine, in a suitable solvent such as benzene or acetonitrile and under suitable reaction conditions, such as a convenient temperature, either by conventional heating or under microwave irradiation for a period of time to ensure the completion of the reaction.

Compounds of Formula (XV) were halo is chloro, bromo or iodo, can be prepared by reacting a compound of Formula (XVI)

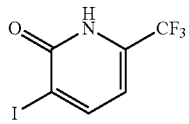

(XVI)

with an N-halo-succinimide, in a suitable solvent, such as N,N-dimethylformamide or acetonitrile, under suitable reaction conditions, such as temperatures typically ranging between 0° C. and 100° C. either by conventional heating or under microwave irradiation for a period of time to ensure the completion of the reaction.

Compounds of Formula (XVI) can be prepared by reacting a compound of Formula (XVII)

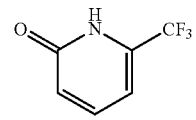

(XVII)

with iodine in the presence of a suitable base, such as potassium carbonate, in a suitable solvent, such as water, under suitable reaction conditions, such as temperatures typically ranging between 0° C. and 100° C. either by conventional heating or under microwave irradiation for a period of time to ensure the completion of the reaction.

Compounds of Formula (IV) wherein -A$^1$=A$^2$- is —CR$^1$=N—, R$^1$ is cyano, R$^2$ is as defined before and L represents a suitable protecting group, such as tert-butyloxycarbonyl, can be prepared by reacting a compound of Formula (XVIII)

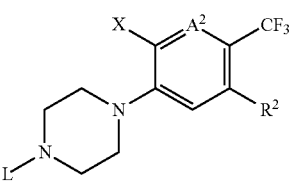

(XVIII)

wherein A$^2$ is nitrogen, R$^2$ is as defined before, L represents a suitable protecting group, such as tert-butyloxycarbonyl, and X represents a sulfonyloxy group, e.g. methylsulfonyloxy, trifluoromethylsulfonyloxy, or methylphenylsulfonyloxy, with zinc cyanide in the presence of a suitable catalyst, such as tetrakis(triphenylphosphine)palladium (0), in a suitable solvent, such as N,N-dimethylformamide under suitable reaction conditions, such as a convenient temperature, either by conventional heating or under microwave irradiation for a period of time to ensure the completion of the reaction.

Compounds of Formula (XVIII) where A$^2$ is nitrogen, R$^2$ is as defined before, L represents a suitable protecting group, such as tert-butyloxycarbonyl, and X represents a sulfonyloxy group, e.g. methylsulfonyloxy, trifluoromethylsulfonyloxy, or methylphenylsulfonyloxy, can be prepared by reacting a compound of Formula (XIX)

(XIX)

wherein A$^2$ is nitrogen, R$^2$ is as defined before and L represents a suitable protecting group, such as tert-butyloxycarbonyl, with a sulfonic anhydride, such as trifluoromethanesulfonic anhydride, in the presence of a suitable base, such as pyridine, in a suitable solvent, such as dichloromethane under suitable reaction conditions, such as a convenient temperature, typically ranging between 0° C. and room temperature.

Compounds of Formula (XIX) where A² is nitrogen, R² is as defined before and L represents a suitable protecting group, such as tert-butyloxycarbonyl, can be prepared by reacting a compound of Formula (XX)

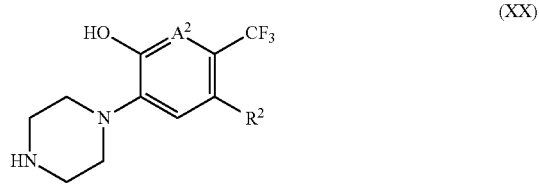

wherein A² is nitrogen and R² is as defined before, with a protecting reagent, such as di-tert-butyldicarbonate, in the presence of a suitable base, such as N,N-diisopropylethylamine, in a suitable solvent, such as dichloromethane under suitable reaction conditions, such as a convenient temperature, typically ranging between 0° C. and room temperature.

Compounds of Formula (XX) where A² is nitrogen and R² is as defined before can be prepared by reacting a compound of Formula (IV) where -A¹=A²- is —CR¹=N—, R¹ is methoxy, R² is as defined before and L represents a suitable protecting group, such as tert-butyloxycarbonyl, with a suitable acid, such as hydrobromic acid, in a suitable solvent, such as water, under suitable reaction conditions, such as a convenient temperature, either by conventional heating or under microwave irradiation for a period of time to ensure the completion of the reaction.

Compounds of Formula (IV) wherein -A¹=A²- is —CR¹=N—, R¹ is $C_{1-3}$alkyl, R² is as defined before and L represents a suitable protecting group, such as tert-butyloxycarbonyl, can be prepared by reacting a compound of Formula (XVIII) with an alkyltin reagent in the presence of a suitable catalyst, such as bis(triphenylphosphine)palladium (II) dichloride, and in the presence of a suitable inorganic salt, such as lithium chloride, in a suitable solvent, such as N,N-dimethylformamide, under suitable reaction conditions, such as a convenient temperature, either by conventional heating or under microwave irradiation for a period of time to ensure the completion of the reaction.

Pharmacology

In order to find antipsychotic compounds active against positive and negative symptoms and cognitive impairment, and having an improved safety profile (low EPS incidence and no metabolic disorders), we have screened for compounds selectively interacting with the dopamine D2 receptor and dissociating fast from this receptor, and further having affinity for the dopamine D3 receptor as well as the serotonin 5-HT-6 receptor. Compounds were first screened for their D2 affinity in a binding assay using [³H]spiperone and human D2L receptor cell membranes. The compounds showing an $IC_{50}$ less than 10 µM were tested in an indirect assay adapted from a method published by Josee E. Leysen and Walter Gommeren, Journal of Receptor Research, 1984, 4(7), 817-845, to evaluate their rate of dissociation.

Some of the compounds were further screened in a panel of more than 50 common G-protein coupled receptors (CEREP) and found to have a clean profile, that is to have low affinity for the tested receptors, with the exception of the dopamine D3 receptor and the serotonin 5-HT6 receptor.

Some of the compounds have been further tested in in vivo models such as the "Antagonism of apomorphine induced agitation test in rats" and found to be active and bio-available.

In view of the aforementioned pharmacology of the compounds of Formula (I), it follows that they are suitable for use as a medicine, in particular for use as an antipsychotic. More especially the compounds are suitable for use as a medicine in the treatment or prevention of schizophrenia, schizophreniform disorder, schizoaffective disorder, delusional disorder, brief psychotic disorder, shared psychotic disorder, psychotic disorder due to a general medical condition, substance-induced psychotic disorder, psychotic disorder not otherwise specified, psychosis associated with dementia, major depressive disorder, dysthymic disorder, premenstrual dysphoric disorder, depressive disorder not otherwise specified, bipolar I disorder, bipolar II disorder, cyclothymic disorder, bipolar disorder not otherwise specified, mood disorder due to a general medical condition, substance-induced mood disorder, mood disorder not otherwise specified; generalized anxiety disorder, obsessive-compulsive disorder, panic disorder, acute stress disorder, post-traumatic stress disorder; mental retardation, pervasive developmental disorders, attention deficit disorders, attention-deficit/hyperactivity disorder, disruptive behaviour disorders; personality disorder of the paranoid type, personality disorder of the schizoid type, personality disorder of the schizotypical type, tic disorders, Tourette's syndrome; substance dependence, substance abuse, substance withdrawal, and trichotillomania. In view of their 5-HT6 antagonistic activity, the compounds of the present invention may further be useful for the treatment or prophylaxis of conditions wherein cognition is impaired; Alzheimer's disease, Parkinson's disease, Huntingdon's disease, Lewy Body Dementia, dementia due to HIV disease, dementia due to Creutzfeldt-Jakob disease; amnestic disorders; mild cognitive impairment; and age-related cognitive decline.

To optimize treatment of patients suffering from a disorder as mentioned in the foregoing paragraph, the compounds of Formula (I) may be administered together with other psychotropic compounds. Thus, in the case of schizophrenia, negative and cognitive symptoms may be targeted.

The present invention also provides a method of treating warm-blooded animals suffering from such disorders, said method comprising the systemic administration of a therapeutic amount of a compound of Formula (I) effective in treating the above described disorders.

The present invention also relates to the use of compounds of Formula (I) as defined hereinabove for the manufacture of a medicament, in particular an antipsychotic medicament, more especially a medicine in the treatment or prevention of schizophrenia, schizophreniform disorder, schizoaffective disorder, delusional disorder, brief psychotic disorder, shared psychotic disorder, psychotic disorder due to a general medical condition, substance-induced psychotic disorder, psychotic disorder not otherwise specified, psychosis associated with dementia, major depressive disorder, dysthymic disorder, premenstrual dysphoric disorder, depressive disorder not otherwise specified, bipolar I disorder, bipolar II disorder, cyclothymic disorder, bipolar disorder not otherwise specified, mood disorder due to a general medical condition, substance-induced mood disorder, mood disorder not otherwise specified, generalized anxiety disorder, obsessive-compulsive disorder, panic disorder, acute stress disorder, post-traumatic stress disorder, mental retardation, pervasive developmental disorders, attention deficit disorders, attention-deficit/hyperactivity disorder, disruptive behaviour disorders, personality disorder of the paranoid type, personality disorder of the schizoid type, personality disorder of the schizotypical type, tic disorders, Tourette's syndrome, substance dependence, substance abuse, substance withdrawal, trichotillomania; and conditions wherein cognition is impaired, Alzheimer's disease, Parkinson's disease, Huntingdon's disease, Lewy Body Dementia, dementia due to HIV disease, dementia due to Creutzfeldt-Jakob disease; amnestic disorders; mild cognitive impairment; and age-related cognitive decline.

Those of skill in the treatment of such diseases could determine the effective therapeutic daily amount from the test results presented hereinafter. An effective therapeutic daily amount would be from about 0.01 mg/kg to about 10 mg/kg body weight, more preferably from about 0.02 mg/kg to about 1 mg/kg body weight.

Pharmaceutical Compositions

The invention also relates to a pharmaceutical composition comprising a pharmaceutically acceptable carrier and, as active ingredient, a therapeutically effective amount of a compound according to Formula (I).

For ease of administration, the subject compounds may be formulated into various pharmaceutical forms for administration purposes. The compounds according to the invention, in particular the compounds according to Formula (I), a pharmaceutically acceptable acid or base addition salt thereof, a stereochemically isomeric form thereof, an N-oxide form thereof and a prodrug thereof, or any subgroup or combination thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, in particular, for administration orally, rectally, percutaneously, by parenteral injection or by inhalation. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, diluents, lubricants, binders, disintegrating agents and the like in the case of powders, pills, capsules and tablets. Because of their ease in administration, tablets and capsules represent the most advantageous oral dosage unit forms in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable solutions, for example, may be prepared in which the carrier comprises saline solution, glucose solution or a mixture of saline and glucose solution. Injectable solutions containing compounds of Formula (I) may be formulated in an oil for prolonged action. Appropriate oils for this purpose are, for example, peanut oil, sesame oil, cottonseed oil, corn oil, soybean oil, synthetic glycerol esters of long chain fatty acids and mixtures of these and other oils. Injectable suspensions may also be prepared in which case appropriate liquid carriers, suspending agents and the like may be employed. Also included are solid form preparations that are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment. Acid or base addition salts of compounds of Formula (I) due to their increased water solubility over the corresponding base or acid form, are more suitable in the preparation of aqueous compositions.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

Since the compounds according to the invention are potent orally administrable compounds, pharmaceutical compositions comprising said compounds for administration orally are especially advantageous.

In order to enhance the solubility and/or the stability of the compounds of Formula (I) in pharmaceutical compositions, it can be advantageous to employ α-, β- or γ-cyclodextrins or their derivatives, in particular hydroxyalkyl substituted cyclodextrins, e.g. 2-hydroxypropyl-β-cyclodextrin. Also co-solvents such as alcohols may improve the solubility and/or the stability of the compounds according to the invention in pharmaceutical compositions.

Depending on the mode of administration, the pharmaceutical composition will comprise from 0.05 to 99% by weight, preferably from 0.1 to 70% by weight, more preferably from 0.1 to 50% by weight of the active ingredient, and, from 1 to 99.95% by weight, preferably from 30 to 99.9% by weight, more preferably from 50 to 99.9% by weight of a pharmaceutically acceptable carrier, all percentages being based on the total weight of the composition.

The following examples are intended to illustrate but not to limit the scope of the present invention.

EXPERIMENTAL PART

Hereinafter, the term "LCMS" means liquid chromatography/mass spectrometry, "GCMS" means gas chromatography/mass spectrometry, "HPLC" means high-performance liquid chromatography, "HPLC" means ultra-performance liquid chromatography, "trans-Pd(OAc)$_2$(Cy$_2$NH)$_2$" means trans-1,1'-bis(dicyclohexylamine)palladium acetate (II), "min." means minutes, "h." means hours, "Rt" means retention time (in minutes), "[M+H]$^+$" means the protonated mass of the free base of the compound, "[M−H]$^-$" means the deprotonated mass of the free base of the compound, "m.p." means melting point.

Microwave assisted reactions were performed in a single-mode reactor: Emrys™ Optimizer microwave reactor (Personal Chemistry A.B., currently Biotage).

Thin layer chromatography (TLC) was carried out on silica gel 60 F254 plates (Merck) using reagent grade solvents. Flash column chromatography was performed on silica gel, particle size 60 Å, mesh=230-400 (Merck) under standard techniques. Automated flash column chromatography was performed using ready-to-connect cartridges from Merck, on irregular silica gel, particle size 15-40 μm (normal phase disposable flash columns) on an SPOT or FLASH system from Armen Instrument.

¹H NMR spectra were recorded either on a Bruker DPX-400 or on a Bruker AV-500 spectrometer with standard pulse sequences, operating at 400 MHz and 500 MHz respectively. Chemical shifts (δ) are reported in parts per million (ppm) downfield from tetramethylsilane (TMS), which was used as internal standard.

A. Preparation of the Intermediates

Example A1

2-Chloro-4-(4-fluoro-phenyl)-5-trifluoromethyl-pyridine

Preparation of Intermediate 1

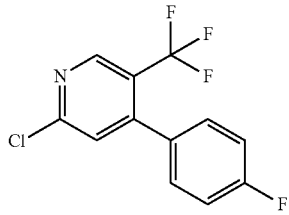 [SMILES: Fc1ccc(-c2cc(Cl)ncc2C(F)(F)F)cc1]

Tetrakis(triphenylphosphine)palladium (0) (0.030 g, 0.00034 mmol) was added to a stirred solution of 2-chloro-4-iodo-5-trifluoromethyl-pyridine (0.350 g, 0.0011 mol) and 4-fluorophenylboronic acid (0.175 g, 0.0013 mol) in a mixture of 1,4-dioxane (3 ml) and a saturated solution of potassium carbonate in water (3 ml). The mixture was heated at 140° C. for 20 min. and at 150° C. for a further 10 min. in a sealed tube, under microwave irradiation. The reaction mixture was diluted with dichloromethane and washed with a saturated solution of sodium carbonate in water. The organic layer was separated, filtered over cotton and the solvents evaporated in vacuo. The crude product was purified by column chromatography (silica; heptane in dichloromethane 20/80 to 50/50). The desired fractions were collected and evaporated in vacuo to yield A1 (0.285 g, 85%). $C_{12}H_6ClF_4N$.

Example A2

4-(6-Chloro-5-trifluoromethyl-pyridin-2-yl)-piperazine-1-carboxylic acid tert-butyl ester Preparation of Intermediate 2

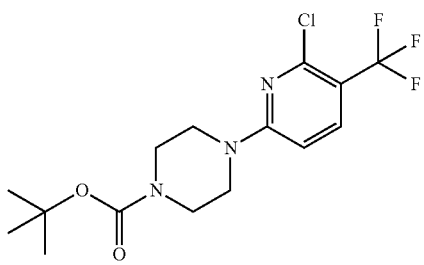 [SMILES: CC(C)(C)OC(=O)N1CCN(c2ccc(C(F)(F)F)c(Cl)n2)CC1]

To a stirred solution of 2,6-dichloro-3-trifluoromethyl-pyridine (0.5 g, 0.0023 mol) and N-Boc-piperazine (0.52 g, 0.0028 mol) in acetonitrile (10 ml) was added diisopropylethylamine (1 ml, 0.0057 mol). The mixture was heated at 140° C. for 20 min. in a sealed tube, under microwave irradiation. The reaction mixture was diluted with dichloromethane and washed with a saturated solution of ammonium chloride in water and water. The organic layer was separated, filtered over cotton and the solvents evaporated in vacuo. The crude product was purified by column chromatography (silica; heptane in dichloromethane 30/70 to 0/100). The desired fractions were collected and evaporated in vacuo to yield A2 (0.72 g, 85%). $C_{15}H_{19}ClF_3N_3O_2$.

¹H NMR (400 MHz, CDCl₃) δ ppm: 1.49 (s, 9 H), 3.48-3.59 (m, 4 H), 3.60-3.69 (m, 4 H), 6.48 (d, J=8.8 Hz, 1 H), 7.69 (d, J=8.8 Hz, 1H).

Example A3

4-(6-Chloro-4-iodo-5-trifluoromethyl-pyridin-2-yl)-piperazine-1-carboxylic acid tert-butyl ester Preparation of Intermediate 3

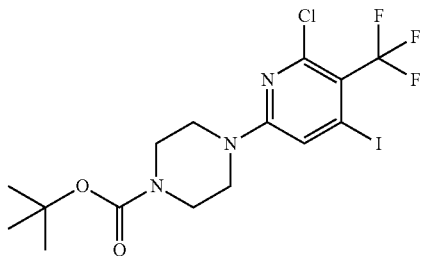 [SMILES: CC(C)(C)OC(=O)N1CCN(c2cc(I)c(C(F)(F)F)c(Cl)n2)CC1]

To a solution 2.5 M of n-butyllithium in hexanes (3.21 ml, 0.0064 mol) in tetrahydrofuran (10 ml) at 0° C., was added 2,2,6,6-tetramethylpiperidine (1.73 ml, 0.0096 mol). The reaction mixture was stirred at room temperature for 1.5 h. The mixture was cooled to −78° C. and then a solution of 4-(6-chloro-5-trifluoromethyl-pyridin-2-yl)-piperazine-1-carboxylic acid tert-butyl ester (A2) (1.174 g, 0.0032 mol) in tetrahydrofuran (10 ml) was added. The mixture was stirred for 1 h. at −78° C. before adding a solution of iodine (0.977 g, 0.0039 mol) in tetrahydrofuran (10 ml). The mixture was stirred at −78° C. for a further 45 min. and then partitioned between a 1 M solution of hydrochloric acid in water and diethyl ether. The mixture was allowed to reach room temperature and then the organic layer was separated, dried (Na₂SO₄), filtered and the solvent evaporated in vacuo. The crude product was purified by column chromatography (silica; ethyl acetate in heptane 0/100 to 5/95). The desired fractions were collected and evaporated in vacuo. The crude product was crystallised from heptane to yield A3 (1.025 g, 65%) as a white solid. $C_{15}H_{18}ClF_3IN_3O_2$.

$^1$H NMR (500 MHz, CDCl$_3$) δ ppm: 1.48 (s, 9 H), 3.44-3.57 (m, 4 H), 3.57-3.68 (m, 4 H), 7.13 (s, 1 H).

Example A4

4-(6-Chloro-4-phenyl-5-trifluoromethyl-pyridin-2-yl)-piperazine-1-carboxylic acid tert-butyl ester Preparation of Intermediate 4

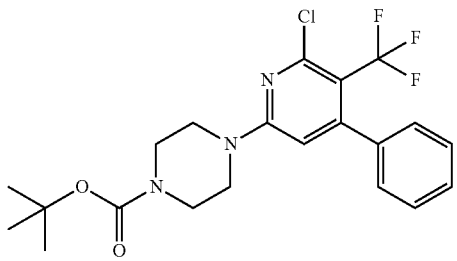 [SMILES: CC(C)(C)OC(=O)N1CCN(c2cc(-c3ccccc3)c(C(F)(F)F)c(Cl)n2)CC1]

trans-Pd(OAc)$_2$(Cy$_2$NH)$_2$ (0.015 g, 0.000026 mol) (prepared by following the procedure described in Tao, B.; Boykin, D. W. Tetrahedron Lett. 2003, 44, 7993-7996) (0.012 g, 0.000020 mol) was added to a stirred solution of 4-(6-chloro-4-iodo-5-trifluoromethyl-pyridin-2-yl)-piperazine-1-carboxylic acid tert-butyl ester (A3) (0.50 g, 0.0010 mol), phenylboronic acid (0.136 g, 0.0011 mol) and potassium phosphate (0.647 g, 0.0031 mol) in ethanol (3 ml). The mixture was stirred at 60° C. for 1 h. in a sealed tube. The mixture was filtered through a pad of diatomaceous earth and the filtrate evaporated in vacuo. The crude product was purified by column chromatography (silica; ethyl acetate in heptane 0/100 to 10/90). The desired fractions were collected and evaporated in vacuo to yield A4 (0.445 g, 99%) as a clear syrup. C$_{21}$H$_{23}$ClF$_3$N$_3$O$_2$.

Example A5

4-(6-Cyano-4-phenyl-5-trifluoromethyl-pyridin-2-yl)-piperazine-1-carboxylic acid tert-butyl ester Preparation of Intermediate 5

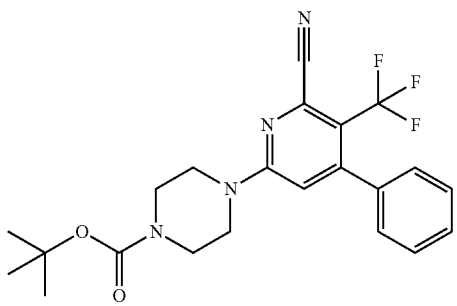 [SMILES: CC(C)(C)OC(=O)N1CCN(c2cc(-c3ccccc3)c(C(F)(F)F)c(C#N)n2)CC1]

Tetrakis(triphenylphosphine)palladium (0) (0.058 g, 0.000050 mol) was added to a stirred solution of 4-(6-chloro-4-phenyl-5-trifluoromethyl-pyridin-2-yl)-piperazine-1-carboxylic acid tert-butyl ester (A4) (0.22 g, 0.00050 mol) and zinc cyanide (0.082 g, 0.00070 mol) in dimethylformamide (5 ml). The mixture was heated at 150° C. for 1.5 h. in a sealed tube, under microwave irradiation. The mixture was partitioned between a mixture of heptane and dichloromethane and water. The organic layer was separated, dried (Na$_2$SO$_4$), filtered and the solvent evaporated in vacuo. The crude product was purified by column chromatography (silica; ethyl acetate in heptane 0/100 to 10/90). The desired fractions were collected and evaporated in vacuo to yield A5 (0.137 g, 64%) as a white solid. C$_{22}$H$_{23}$F$_3$N$_4$O$_2$.

$^1$H NMR (400 MHz, CDCl$_3$) δ ppm: 1.49 (s, 9 H), 3.45-3.60 (m, 4 H), 3.69 (br. s., 4 H), 6.60 (s, 1 H), 7.19-7.32 (m, 2 H), 7.37-7.49 (m, 3 H).

Example A6

4-(6-Methoxy-4-phenyl-5-trifluoromethyl-pyridin-2-yl)-piperazine-1-carboxylic acid tert-butyl ester Preparation of Intermediate 6

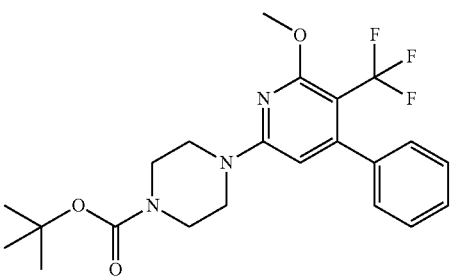 [SMILES: COc1nc(N2CCN(C(=O)OC(C)(C)C)CC2)cc(-c2ccccc2)c1C(F)(F)F]

A 25% solution of sodium methanolate in methanol (2.53 ml, 0.00060 mol) was added to a stirred solution of 4-(6-chloro-4-phenyl-5-trifluoromethyl-pyridin-2-yl)-piperazine-1-carboxylic acid tert-butyl ester (A4) (0.22 g, 0.00050 mol) in methanol (2 ml). The mixture was heated at 125° C. for 30 min. in a sealed tube, under microwave irradiation. The mixture was diluted with dichloromethane and extracted with a 1N solution of hydrochloric acid in water. The organic layer was separated, dried (Na$_2$SO$_4$), filtered and the solvent evaporated in vacuo. The crude product was purified by column chromatography (silica; ethyl acetate in heptane 0/100 to 5/95). The desired fractions were collected and evaporated in vacuo to yield A6 (0.083 g, 38%) as a white solid. C$_{22}$H$_{26}$F$_3$N$_3$O$_3$.

$^1$H NMR (400 MHz, CDCl$_3$) δ ppm: 1.48 (s, 9 H), 3.49-3.56 (m, 4 H), 3.57-3.64 (m, 4 H), 3.98 (s, 3 H), 5.94 (s, 1 H), 7.21-7.30 (m, 2 H), 7.33-7.41 (m, 3 H).

Example A7

4-(5-Chloro-pyridin-3-yl)-piperazine-1-carboxylic acid tert-butyl ester

Preparation of Intermediate 7

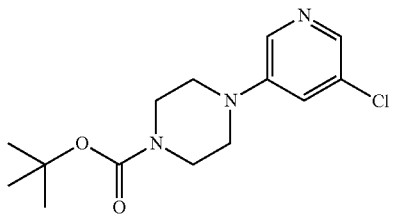 [SMILES: CC(C)(C)OC(=O)N1CCN(c2cncc(Cl)c2)CC1]

N-Boc-piperazine (0.52 g, 0.0028 mol) was added to a stirred solution of 3-bromo-5-chloro-pyridine (1 g, 0.0052 mol), tris(dibenzylideneacetone)dipalladium (0) chloroform adduct (0.269 g, 0.00026 mol), (R)-(+)-2,2'-bis(diphenylphosphino)-1,1'-binaphthyl (0.324 g, 0.00052 mol) and sodium tert-butoxide (1 g, 0.010 mol) in toluene (20 ml) under N$_2$ flow. The mixture was heated at 100° C. for 18 h. and then filtered through a pad of diatomaceous earth. The filtrate was extracted with water. The organic layer was separated, dried (Na$_2$SO$_4$), filtered and the solvent evaporated in vacuo. The crude product was purified by column chromatography (silica; ethyl acetate in heptane 25/75). The desired fractions were collected and evaporated in vacuo to yield A7 (1.3 g, 88%). C$_{14}$H$_{20}$ClN$_3$O$_2$.

Example A8

4-(5-Phenyl-pyridin-3-yl)-piperazine-1-carboxylic acid tert-butyl ester

Preparation of Intermediate 8

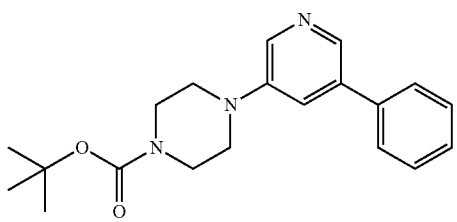 [SMILES: CC(C)(C)OC(=O)N1CCN(c2cncc(-c3ccccc3)c2)CC1]

A mixture of 4-(5-chloro-pyridin-3-yl)-piperazine-1-carboxylic acid tert-butyl ester (A7) (1.3 g, 0.0044 mol), phenylboronic acid (0.798 g, 0.0065 mol), 2-dicyclohexylphosphino-2',4',6'-triisopropylbiphenyl (0.416 g, 0.00087 mol), palladium 10% on activated charcoal (0.116 g) and potassium carbonate (2.413 g, 0.017 mol) in a mixture of N,N-dimethylacetamide (20 ml) and water (2 ml) under N$_2$, was heated at 85° C. for 18 h. The mixture was filtered through a pad of diatomaceous earth. The filtrate was diluted with ethyl acetate and extracted with water. The organic layer was separated, dried (MgSO$_4$), filtered and the solvent evaporated in vacuo. The crude product was purified by column chromatography (silica; ethyl acetate in heptane 1/99). The desired fractions were collected and evaporated in vacuo to yield A8 (1.3 g, 88%). C$_{20}$H$_{25}$N$_3$O$_2$.

Example A9

4-(6-Iodo-5-phenyl-pyridin-3-yl)-piperazine-1-carboxylic acid tert-butyl ester

Preparation of Intermediate 9

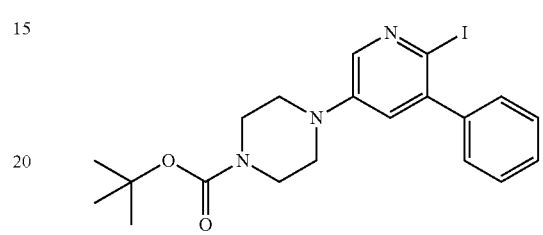

To a stirred solution of 4-(5-phenyl-pyridin-3-yl)-piperazine-1-carboxylic acid tert-butyl ester (A8) (1 g, 0.0029 mol) in methanol (10 ml), silver trifluoroacetate (0.784 g, 0.0035 mol) and iodine (0.897 g, 0.0035 mol) were added. The mixture was stirred at room temperature for 18 h. After this period, further silver trifluoroacetate (0.784 g, 0.0035 mol) and iodine (0.897 g, 0.0035 mol) were added and the mixture was stirred for a further 5 h. The mixture was filtered and a saturated solution of sodium thiosulfate in water was added to the filtrate. The mixture was stirred at room temperature for 5 min. and then diluted with dichloromethane. The mixture was extracted with water and brine. The organic layer was separated, dried (MgSO$_4$), filtered and the solvent evaporated in vacuo. The crude product was purified by column chromatography (silica; ethyl acetate in dichloromethane 10/90). The desired fractions were collected and evaporated in vacuo to yield A9 (0.280 g, 16%) as a syrup. C$_{20}$H$_{24}$IN$_3$O$_2$.

$^1$H NMR (500 MHz, CDCl$_3$) δ ppm: 1.48 (s, 9 H), 3.12-3.24 (m, 4 H), 3.53-3.63 (m, 4 H), 7.04 (d, J=3.2 Hz, 1 H), 7.30-7.40 (m, 2 H), 7.39-7.50 (m, 3 H), 8.05 (d, J=3.2 Hz, 1 H).

Example A10

4-(5-Phenyl-6-trifluoromethyl-pyridin-3-yl)-piperazine-1-carboxylic acid tert-butyl ester Preparation of Intermediate 10

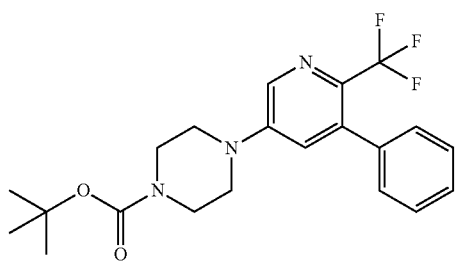 [SMILES: CC(C)(C)OC(=O)N1CCN(c2cnc(C(F)(F)F)c(-c3ccccc3)c2)CC1]

Copper (I) iodide (0.164 g, 0.00086 mol) and methyl fluorosulfonyldifluoroacetate (0.108 ml, 0.00086 mol) were added to a stirred solution of 4-(6-iodo-5-phenyl-pyridin-3-yl)-piperazine-1-carboxylic acid tert-butyl ester (A9) (0.2 g, 0.00043 mol) in dimethylformamide (5 ml) under $N_2$. The mixture was heated at 90° C. for 4 h. in a sealed tube and after cooling was diluted with diethyl ether and washed with a 12% solution of ammonium in water. The organic layer was separated, dried ($Na_2SO_4$), filtered and the solvent evaporated in vacuo. The crude product was purified by column chromatography (silica; ethyl acetate in heptane 5/95). The desired fractions were collected and evaporated in vacuo to yield A10 (0.06 g, 34%) as a syrup. $C_{21}H_{24}F_3N_3O_2$.

Example A11

3-Iodo-6-trifluoromethyl-1H-pyridin-2-one

Preparation of Intermediate 11

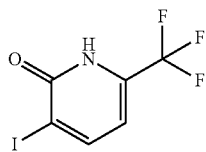 [SMILES: O=c1[nH]c(C(F)(F)F)ccc1I]

6-Trifluoromethyl-1H-pyridin-2-one (5 g, 0.031 mol) and iodine (11.67 g, 0.046 mol) were added to a stirred solution of potassium carbonate (12.71 g, 0.092 mol) in water. The mixture was stirred at room temperature for 24 h. A saturated solution of sodium thiosulfate in water was added and the mixture was stirred at room temperature for 5 min. The mixture was acidified by a 1 N hydrochloric acid solution in water addition and extracted with dichloromethane. The organic layer was separated, dried ($MgSO_4$), filtered and the solvent evaporated in vacuo. The crude product was purified by column chromatography (silica; ethyl acetate in heptane 20/80). The desired fractions were collected and evaporated in vacuo to yield A11 (6.1 g, 69%). $C_6H_3F_3INO$.
$^1$H NMR (400 MHz, $CDCl_3$) δ ppm: 6.59 (d, J=7.4 Hz, 1 H) 8.19 (d, J=7.4 Hz, 1 H), 10.55 (br. s., 1H).

Example A12

5-Chloro-3-iodo-6-trifluoromethyl-1H-pyridin-2-one

Preparation of Intermediate 12

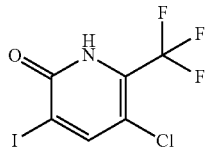 [SMILES: O=c1[nH]c(C(F)(F)F)c(Cl)cc1I]

N-Chlorosuccinimide (8.32 g, 0.062 mol) was added to a stirred solution of 3-iodo-6-trifluoromethyl-1H-pyridin-2-one (6 g, 0.021 mol) in N,N-dimethylformamide (30 ml). The mixture was stirred at room temperature for 24 h. More N-chlorosuccinimide (4.16 g, 0.031 mol) was added and the mixture stirred for a further 48 h. The solvent was evaporated in vacuo. The residue was dissolved in dichloromethane and extracted with water. The organic layer was separated, dried ($MgSO_4$), filtered and the solvent evaporated in vacuo. The crude product was purified by column chromatography (silica; ethyl acetate in heptane 2/98). The desired fractions were collected and evaporated in vacuo to yield A12 (2.95 g, 44%). $C_6H_2ClF_3INO$.

Example A13

3-Chloro-5-iodo-6-methoxy-2-trifluoromethyl-pyridine

Preparation of Intermediate 13

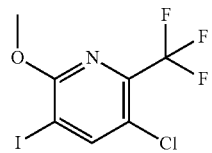

Silver carbonate (2.58 g, 0.0093 mol) and methyl iodide (1.16 ml, 0.019 mol) were added to a stirred solution of 5-chloro-3-iodo-6-trifluoromethyl-1H-pyridin-2-one (A12) (3 g, 0.0093 mol) in benzene (15 ml). The mixture was stirred at 50° C. for 16 h. and was then diluted with ethyl acetate and filtered off. The filtrate was extracted with water. The organic layer was separated, dried ($Na_2SO_4$), filtered and the solvent evaporated in vacuo. The crude product was purified by column chromatography (silica; ethyl acetate in heptane 2/98). The desired fractions were collected and evaporated in vacuo to yield A13 (1.2 g, 38%) as an oil. $C_7H_4ClF_3INO$.
$^1$H NMR (500 MHz, $CDCl_3$) δ ppm: 4.01 (s, 3 H), 8.16 (s, 1 H).

Example A14

4-(5-Chloro-2-methoxy-6-trifluoromethyl-pyridin-3-yl)-piperazine-1-carboxylic acid tert-butyl ester Preparation of Intermediate 14

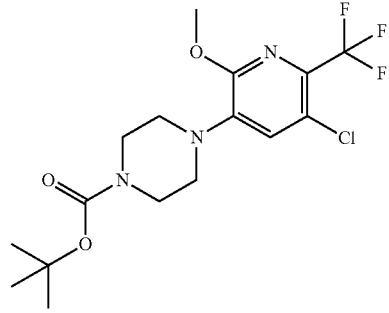 [SMILES: COc1nc(C(F)(F)F)c(Cl)cc1N1CCN(C(=O)OC(C)(C)C)CC1]

N-Boc-piperazine was added (0.828 g, 0.0044 mol) to a stirred solution of 3-chloro-5-iodo-6-methoxy-2-trifluoromethyl-pyridine (A13) (1 g, 0.0030 mol), palladium (II) acetate (0.033 g, 0.00015 mol), (R)-(+)-2,2'-bis(diphenylphosphino)-1,1'-binaphthyl (0.0277 g, 0.00044 mol) and cesium carbonate (1.93 g, 0.0059 mol) in toluene (15 ml) under $N_2$. The mixture was heated at 85° C. for 18 h., then filtered through a pad of diatomaceous earth and evaporated in vacuo.

The crude product was purified by column chromatography (silica; ethyl acetate in heptane 1/99). The desired fractions were collected and evaporated in vacuo to yield A14 (0.98 g, 84%). $C_{16}H_{21}ClF_3N_3O_3$.

$^1$H NMR (500 MHz, CDCl$_3$) δ ppm: 1.49 (s, 9 H), 3.03-3.19 (m, 4 H), 3.54-3.66 (m, 4 H); 4.02 (s, 3 H), 7.04 (s, 1 H).

Example A15

4-(2-Methoxy-5-phenyl-6-trifluoromethyl-pyridin-3-yl)-piperazine-1-carboxylic acid tert-butyl ester Preparation of Intermediate 15

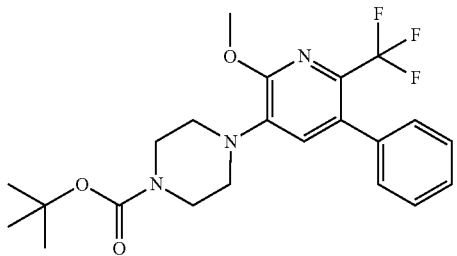 [SMILES: COc1nc(C(F)(F)F)c(-c2ccccc2)cc1N1CCN(C(=O)OC(C)(C)C)CC1]

A mixture of 4-(5-chloro-2-methoxy-6-trifluoromethyl-pyridin-3-yl)-piperazine-1-carboxylic acid tert-butyl ester (A14) (0.98 g, 0.0025 mol), phenylboronic acid (0.906 g, 0.0074 mol), 2-dicyclohexylphosphino-2',4',6'-triisopropylbiphenyl (0.472 g, 0.00099 mol), palladium 10% on activated charcoal (0.132 g) and potassium carbonate (1.369 g, 0.010 mol) in a mixture of N,N-dimethylacetamide (12 ml) and water (1.2 ml) under N$_2$, was heated at 90° C. for 18 h. The mixture was filtered through a pad of diatomaceous earth. The filtrate was diluted with ethyl acetate and extracted with water. The organic layer was separated, dried (MgSO$_4$), filtered and the solvent evaporated in vacuo. The crude product was purified by column chromatography (silica; ethyl acetate in heptane 1/99). The desired fractions were collected and evaporated in vacuo to yield A15 (0.95 g, 88%) as a syrup. $C_{22}H_{26}F_3N_3O_3$.

Example A16

4-[5-(4-Fluoro-phenyl)-2-methoxy-6-trifluoromethyl-pyridin-3-yl]-piperazine-1-carboxylic acid tert-butyl ester Preparation of Intermediate 16

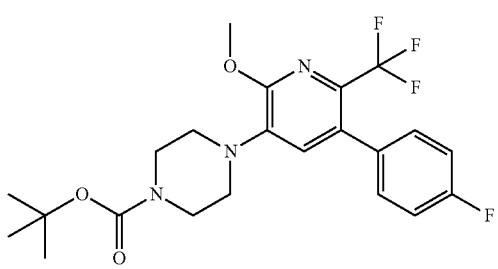 [SMILES: COc1nc(C(F)(F)F)c(-c2ccc(F)cc2)cc1N1CCN(C(=O)OC(C)(C)C)CC1]

Intermediate 16 was prepared from intermediate A14 according to an analogous protocol as was used for the synthesis of intermediate 15 as a syrup. $C_{22}H_{25}F_4N_3O_3$.

$^1$H NMR (500 MHz, CDCl$_3$) δ ppm 1.47 (s, 9 H), 3.08-3.13 (m, 4 H), 3.57-3.64 (m, 4 H), 4.07 (s, 3 H), 6.90 (s, 1 H), 7.09 (t, J=8.7 Hz, 2 H), 7.24-7.29 (m, 2 H).

Example A17

5-Phenyl-3-piperazin-1-yl-6-trifluoromethyl-pyridin-2-ol

Preparation of Intermediate 17

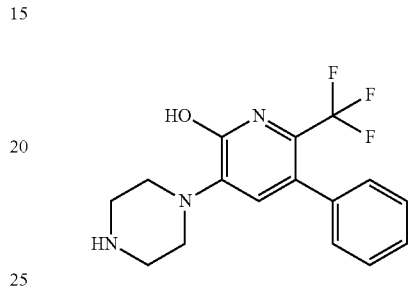

A mixture of 4-(2-methoxy-5-phenyl-6-trifluoromethyl-pyridin-3-yl)-piperazine-1-carboxylic acid tert-butyl ester (A15) (0.70 g, 0.0016 mol) in a 47% solution of hydrobromic acid in water (10 ml) was heated at 100° C. for 4 h. in a sealed tube. The solvent was evaporated in vacuo and the crude product was precipitated from diethyl ether to yield A17 (0.62 g, 96%) as a white solid. $C_{16}H_{16}F_3N_3O$.HBr.

$^1$H NMR (400 MHz, DMSO-d$_6$) δ ppm: 3.24 (br. s., 4 H), 3.39 (br. s., 4 H), 7.01 (br. s., 1 H), 7.29-7.37 (m, 2 H), 7.38-7.50 (m, 3 H), 8.76 (br. s., 2 H), 12.10 (br. s., 1 H).

Example A18

4-(2-Hydroxy-5-phenyl-6-trifluoromethyl-pyridin-3-yl)-piperazine-1-carboxylic acid tert-butyl ester Preparation of Intermediate 18

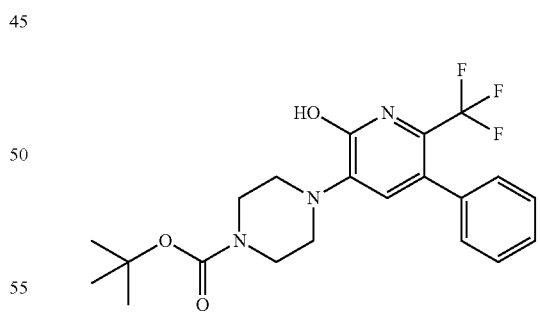

Di-tert-butyldicarbonate (0.404 g, 0.0019 mol) and N,N-diisopropylethylamine (0.43 ml, 0.0025 mol) were added to a stirred suspension of 5-phenyl-3-piperazin-1-yl-6-trifluoromethyl-pyridin-2-ol (A17) (0.5 g, 0.0012 mol) in dichloromethane (25 ml). The mixture was stirred at room temperature for 3 h. The solvent was evaporated in vacuo. The crude product was purified by column chromatography (silica; ethyl acetate). The desired fractions were collected and evaporated in vacuo to yield A18 (0.38 g, 72%) as a white solid. $C_{21}H_{24}F_3N_3O_3$.

¹H NMR (500 MHz, chloroform-d) δ ppm: 1.47 (s, 9 H), 3.22-3.29 (m, 4 H), 3.57-3.62 (m, 4 H); 6.53 (s, 1 H), 7.27-7.32 (m, 2 H), 7.34-7.46 (m, 3 H), 10.10 (br. s, 1 H).

Example A19

4-(5-Phenyl-2-trifluoromethanesulfonyloxy-6-trifluoromethyl-pyridin-3-yl)-piperazine-1-carboxylic acid tert-butyl ester Preparation of Intermediate 19

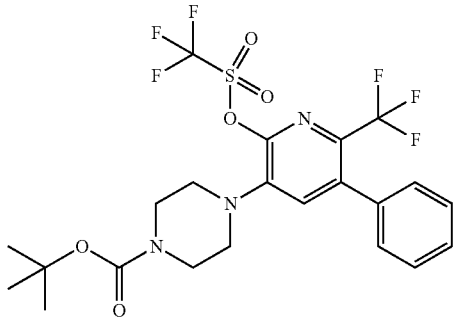 [SMILES: CC(C)(C)OC(=O)N1CCN(c2cc(-c3ccccc3)c(C(F)(F)F)nc2OS(=O)(=O)C(F)(F)F)CC1]

Trifluoromethanesulfonic anhydride (0.297 ml, 0.0018 mol) and pyridine (0.362 ml, 0.0045 mol) were added to a stirred suspension of 4-(2-hydroxy-5-phenyl-6-trifluoromethyl-pyridin-3-yl)-piperazine-1-carboxylic acid tert-butyl ester (A18) (0.38 g, 0.0009 mol) in dichloromethane (25 ml) at 0° C. The mixture was allowed to warm to room temperature, stirred for 16 h., was then diluted with dichloromethane and extracted with a saturated solution of ammonium chloride in water. The organic layer was separated, dried (MgSO$_4$), filtered and the solvent evaporated in vacuo. The crude product was purified by column chromatography (silica; ethyl acetate in heptane 2/98). The desired fractions were collected and evaporated in vacuo to yield A19 (0.395 g, 79%). $C_{22}H_{23}F_6N_3O_5S$.

Example A20

4-(2-Cyano-5-phenyl-6-trifluoromethyl-pyridin-3-yl)-piperazine-1-carboxylic acid tert-butyl Preparation of Intermediate 20

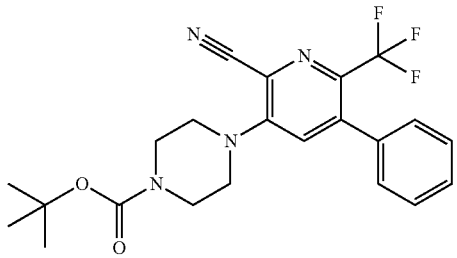 [SMILES: CC(C)(C)OC(=O)N1CCN(c2cc(-c3ccccc3)c(C(F)(F)F)nc2C#N)CC1]

A mixture of zinc cyanide (0.085 g, 0.00072 mol) and tetrakis(triphenylphosphine)palladium (0) (0.063 g, 0.000054 mol) was added to a stirred solution of 4-(5-phenyl-2-trifluoromethanesulfonyloxy-6-trifluoromethyl-pyridin-3-yl)-piperazine-1-carboxylic acid tert-butyl ester (A19) (0.20 g, 0.00036 mol) in N,N-dimethylformamide (5 ml) under N$_2$. The mixture was heated at 90° C. for 5 h. in a sealed tube. The mixture was diluted with dichloromethane and extracted with a saturated solution of sodium hydrogen carbonate in water. The organic layer was separated, dried (MgSO$_4$), filtered and the solvent evaporated in vacuo. The crude product was purified by column chromatography (silica; 7M solution of ammonia in methanol in dichloromethane 0/100 to 1/99). The desired fractions were collected and evaporated in vacuo to yield A20 (0.145 g, 93%) as a syrup. $C_{22}H_{23}F_3N_4O_2$.

Example A21

4-(2-Methyl-5-phenyl-6-trifluoromethyl-pyridin-3-yl)-piperazine-1-carboxylic acid tert-butyl ester Preparation of Intermediate 21

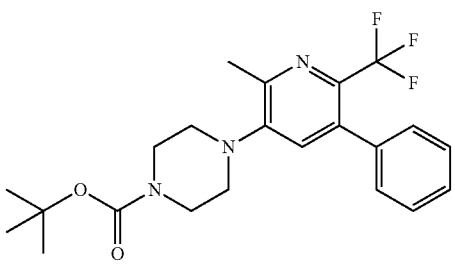 [SMILES: Cc1nc(C(F)(F)F)c(-c2ccccc2)cc1N1CCN(C(=O)OC(C)(C)C)CC1]

A mixture of bis(triphenylphosphine)palladium (II) dichloride (0.013 g, 0.000018 mol) and lithium chloride (0.076 g, 0.0018 mol), and tetramethyltin (0.119 ml, 0.00072 mol) were added to a stirred solution of 4-(5-phenyl-2-trifluoromethanesulfonyloxy-6-trifluoromethyl-pyridin-3-yl)-piperazine-1-carboxylic acid tert-butyl ester (A19) (0.20 g, 0.00036 mol) in N,N-dimethylformamide (5 ml) under N$_2$. The mixture was heated at 130° C. for 2 h. in a sealed tube. After this period, the mixture was filtered through a pad of diatomaceous earth. The filtrate was diluted with dichloromethane and extracted with water. The organic layer was separated, dried (MgSO$_4$), filtered and the solvent evaporated in vacuo. The crude product was purified by column chromatography (silica; ethyl acetate in dichloromethane 0/100 to 40/60). The desired fractions were collected and evaporated in vacuo to yield A21 (0.115 g, 76%) as a syrup. $C_{22}H_{26}F_3N_4O_2$.

B. Preparation of the Final Compounds

Example B1

1-[4-(4-Fluoro-phenyl)-5-trifluoromethyl-pyridin-2-yl]-piperazine

Preparation of Compound 1

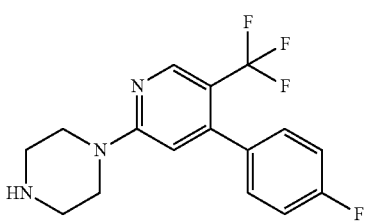 [SMILES: Fc1ccc(-c2cc(N3CCNCC3)ncc2C(F)(F)F)cc1]

A solution of 2-chloro-4-(4-fluoro-phenyl)-5-trifluoromethyl-pyridine (A1) (0.095 g, 0.00035 mol) and piperazine (0.237 g, 0.0028 mol) in acetonitrile (3 ml) was heated at 150° C. for 20 min., under microwave irradiation. The reaction mixture was poured onto a mixture of a saturated solution of sodium carbonate in water and water and extracted with dichloromethane. The organic layer was separated, filtered over cotton and the solvents evaporated in vacuo. The crude product was purified by column chromatography (silica; 7M solution of ammonia in methanol in dichloromethane 0/100 to 1/99). The desired fractions were collected and evaporated in vacuo to yield B1 (0.104 g, 93%) as a white solid.

$^1$H NMR (500 MHz, chloroform-d) δ ppm: 2.90-3.04 (m, 4 H), 3.58-3.69 (m, 4 H), 6.43 (s, 1 H), 7.06-7.14 (m, 2 H), 7.27-7.34 (m, 2 H), 8.46 (s, 1 H).

$^1$H NMR (500 MHz, CDCl$_3$) δ ppm: 1.71 (s, 1 H), 2.98 (t, J=4.9 Hz, 4 H), 3.63 (t, J=5.2 Hz, 4 H), 6.43 (s, 1 H), 7.10 (t, J=8.7 Hz, 2 H), 7.29 (dd, J=8.5, 5.3 Hz, 2 H), 8.46 (s, 1 H).

Example B2

4-Phenyl-6-piperazin-1-yl-3-trifluoromethyl-pyridine-2-carbonitrile

Preparation of Compound 2

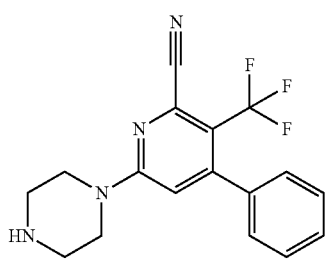 [SMILES: N#Cc1nc(N2CCNCC2)cc(-c2ccccc2)c1C(F)(F)F]

Trifluoroacetic acid (1 ml) was added to a stirred solution of 4-(6-chloro-4-phenyl-5-trifluoromethyl-pyridin-2-yl)-piperazine-1-carboxylic acid tert-butyl ester (A5) in dichloromethane (5 ml). The mixture was stirred at room temperature for 3 h. The solvents were evaporated in vacuo. The crude product was crystallised from diisopropyl ether/ethyl acetate to yield B2 (0.085 g, 85%) as a white solid. $C_{17}H_{15}F_3N_4 \cdot CF_3CO_2H$.

$^1$H NMR (500 MHz, DMSO-d$_6$) δ ppm: 3.14-3.27 (m, 4 H), 3.89-4.02 (m, 4 H), 7.16 (s, 1 H), 7.27-7.41 (m, 2 H), 7.42-7.58 (m, 3 H), 8.92 (br. s., 2 H).

$^1$H NMR (500 MHz, DMSO-d$_6$) δ ppm: 3.16-3.25 (m, 4 H), 3.88-3.97 (m, 4 H), 7.17 (s, 1 H), 7.36 (dd, J=6.5, 2.7 Hz, 2 H), 7.45-7.54 (m, 3 H), 8.93 (br. s., 2 H).

Example B3

1-(6-Methoxy-4-phenyl-5-trifluoromethyl-pyridin-2-yl)-piperazine

Preparation of Compound 3

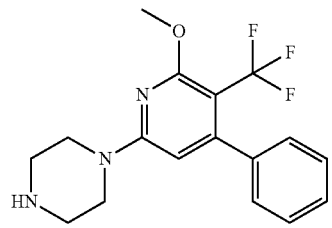 [SMILES: COc1nc(N2CCNCC2)cc(-c2ccccc2)c1C(F)(F)F]

Trifluoroacetic acid (0.5 ml) was added to a stirred solution of 4-(6-methoxy-4-phenyl-5-trifluoromethyl-pyridin-2-yl)-piperazine-1-carboxylic acid tert-butyl ester (A6) (0.083 g, 0.00019 mol) in dichloromethane (5 ml). The mixture was stirred at room temperature for 16 h. The reaction mixture was diluted with further dichloromethane and extracted with a saturated solution of sodium hydrogen carbonate. The organic layer was separated, dried (Na$_2$SO$_4$), filtered and the solvent evaporated in vacuo. The crude product was purified by column chromatography (silica; 7M solution of ammonia in methanol in dichloromethane 0/100 to 5/95). The desired fractions were collected and evaporated in vacuo and the residue dissolved in diisopropyl ether and converted into its hydrochloric acid salt by addition of a 4M solution of hydrochloric acid in diethyl ether to yield B3 (0.032 g, 45%) as a white solid. $C_{17}H_{18}F_3N_3O \cdot HCl$.

$^1$H NMR (400 MHz, DMSO-d$_6$) δ ppm: 3.10-3.22 (m, 4 H), 3.81-3.90 (m, 4 H), 3.94 (s, 3 H), 6.27 (s, 1 H), 7.19-7.34 (m, 2 H), 7.35-7.55 (m, 3 H), 9.14 (br. s., 2 H).

Example B4

1-(5-Phenyl-6-trifluoromethyl-pyridin-3-yl)-piperazine

Preparation of Compound 4

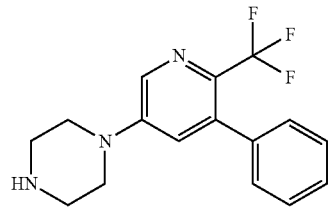 [SMILES: FC(F)(F)c1ncc(N2CCNCC2)cc1-c1ccccc1]

Trifluoroacetic acid (1.25 ml) was added to a stirred solution of 4-(5-phenyl-6-trifluoromethyl-pyridin-3-yl)-piperazine-1-carboxylic acid tert-butyl ester (A10) (0.060 g, 0.00015 mol) in dichloromethane (5 ml). The mixture was stirred at room temperature for 2 h. The solvents were evaporated in vacuo. The residue was precipitated from diethyl ether to yield B4 (0.040 g, 64%) as a white solid. $C_{1-16}H_{16}F_3N_3 \cdot CF_3CO_2H$.

$^1$H NMR (400 MHz, DMSO-$d_6$) δ ppm: 3.25-3.34 (m, 4 H), 3.65-3.75 (m, 4 H), 7.38 (d, J=2.5 Hz, 1 H), 7.40-7.45 (m, 2 H), 7.47-7.62 (m, 3 H), 8.53 (d, J=2.8 Hz, 1 H), 8.90 (br. s., 2 H).

Example B5

1-(2-Methoxy-5-phenyl-6-trifluoromethyl-pyridin-3-yl)-piperazine

Preparation of Compound 5

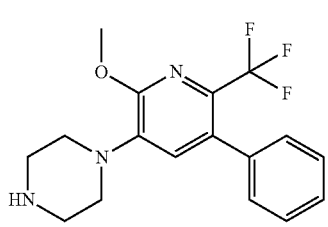 [SMILES: COc1nc(C(F)(F)F)c(-c2ccccc2)cc1N1CCNCC1]

Trifluoroacetic acid (1.25 ml) was added to a stirred solution of 4-(2-methoxy-5-phenyl-6-trifluoromethyl-pyridin-3-yl)-piperazine-1-carboxylic acid tert-butyl ester (A15) (0.180 g, 0.00041 mol) in dichloromethane (5 ml). The mixture was stirred at room temperature for 2 h. The solvents were evaporated in vacuo. The residue was precipitated from diethyl ether to yield B5 (0.175 g, 94%) as a white solid. $C_{17}H_{18}F_3N_3O \cdot CF_3CO_2H$.

$^1$H NMR (400 MHz, DMSO-$d_6$) δ ppm: 3.22-3.28 (m, 4 H), 3.35-3.41 (m, 4 H), 3.99 (s, 3 H), 7.17 (s, 1 H), 7.32-7.38 (m, 2 H), 7.42-7.50 (m, 3 H), 8.82 (br. s., 2 H).

Example B6

1-[5-(4-Fluoro-phenyl)-2-methoxy-6-trifluoromethyl-pyridin-3-yl]-piperazine

Preparation of Compound 6

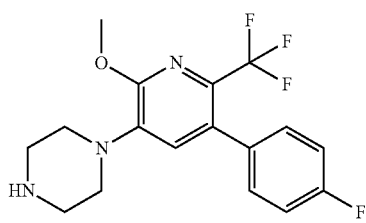 [SMILES: COc1nc(C(F)(F)F)c(-c2ccc(F)cc2)cc1N1CCNCC1]

Compound 6 was prepared from intermediate A16 according to an analogous protocol as was used for the synthesis of compound 5. $C_{17}H_{17}F_4N_3O \cdot CF_3CO_2H$.

$^1$H NMR (500 MHz, DMSO-$d_6$) δ ppm: 3.22-3.28 (m, 4 H), 3.35-3.42 (m, 4 H), 3.98 (s, 3 H), 7.18 (s, 1 H), 7.30 (t, J=8.8 Hz, 2 H), 7.40 (dd, J=8.7, 5.5 Hz, 2 H), 8.78 (br. s., 2 H).

Example B7

5-Phenyl-3-piperazin-1-yl-6-trifluoromethyl-pyridine-2-carbonitrile

Preparation of Compound 7

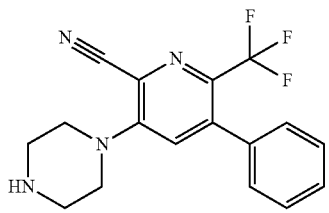 [SMILES: N#Cc1nc(C(F)(F)F)c(-c2ccccc2)cc1N1CCNCC1]

Trifluoroacetic acid (2 ml) was added to a stirred solution of 4-(2-cyano-5-phenyl-6-trifluoromethyl-pyridin-3-yl)-piperazine-1-carboxylic acid tert-butyl (A20) (0.145 g, 0.00034 mol) in dichloromethane (8 ml). The mixture was stirred at room temperature for 2 h. After this period, the solvents were evaporated in vacuo. The residue was precipitated from diethyl ether to yield B7 (0.135 g, 90%) as a white solid. $C_{17}H_{15}F_3N_4 \cdot CF_3CO_2H$.

$^1$H NMR (400 MHz, DMSO-$d_6$) δ ppm: 3.27-3.32 (m, 4 H), 3.63-3.74 (m, 4 H), 7.41 (dd, J=6.5, 2.8 Hz, 2 H), 7.48-7.56 (m, 3 H), 7.71 (s, 1 H), 8.90 (br. s., 2H).

Example B8

1-(2-Methyl-5-phenyl-6-trifluoromethyl-pyridin-3-yl)-piperazine

Preparation of Compound 8

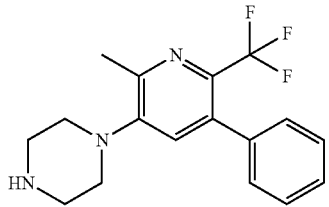 [SMILES: Cc1nc(C(F)(F)F)c(-c2ccccc2)cc1N1CCNCC1]

A solution of 4-(2-methyl-5-phenyl-6-trifluoromethyl-pyridin-3-yl)-piperazine-1-carboxylic acid tert-butyl ester (A21) (0.115 g, 0.00027 mol) in a 4 M solution of hydrochloric acid in 1,4-dioxane was stirred at room temperature for 2 h. The solvents were evaporated in vacuo. The residue was precipitated from diethyl ether to yield B8 (0.09 g, 92%) as a white solid. $C_{17}H_{18}F_3N_3 \cdot HCl$.

$^1$H NMR (400 MHz, DMSO-$d_6$) δ ppm: 2.56 (s, 3 H), 3.25 (m, 8 H), 7.35 (s, 1 H), 7.35-7.39 (m, 2 H), 7.43-7.51 (m, 3 H), 9.20 (br. s., 2 H)

C. Analytical Part

Melting Points:

Values are peak values, and are obtained with experimental uncertainties that are commonly associated with this analytical method.

For a number of compounds, melting points were determined in open capillary tubes on a Mettler FP62 apparatus. Melting points were measured with a temperature gradient of 10° C./minute. Maximum temperature was 300° C. The melting point was read from a digital display.

Nuclear Magnetic Resonance (NMR)

$^1$H NMR spectra were recorded either on a Bruker DPX-400 or on a Bruker AV-500 spectrometer with standard pulse sequences, operating at 400 MHz and 500 MHz respectively. Chemical shifts (δ) are reported in parts per million (ppm) downfield from tetramethylsilane (TMS), which was used as internal standard.

LCMS-methods:

For LCMS-characterization of the compounds of the present invention, the following methods were used.

General Procedure A

The HPLC measurement was performed using a HP 1100 from Agilent Technologies comprising a pump (quaternary or binary) with degasser, an autosampler, a column oven, a diode-array detector (DAD) and a column as specified in the respective methods below. Flow from the column was split to a MS spectrometer. The MS detector was configured with an electrospray ionization source. Nitrogen was used as the nebulizer gas. The source temperature was maintained at 140° C. Data acquisition was performed with MassLynx-Openlynx software.

General Procedure B

The HPLC measurement was performed using a HP 1100 from Agilent Technologies comprising a binary pump with degasser, an autosampler, a column oven, a diode-array detector (DAD) and a column as specified in the respective methods below. Flow from the column was split to a MS spectrometer. The MS detector was configured with an ESCI dual ionization source (electrospray combined with atmospheric pressure chemical ionization). Nitrogen was used as the nebulizer gas. The source temperature was maintained at 100° C. Data acquisition was performed with Chemsation-Agilent Data Browser software.

Method 1

In addition to the general procedure A: Reversed phase HPLC was carried out on an XDB-C18 cartridge (1.8 μm, 2.1×30 mm) from Agilent, at 60° C. with a flow rate of 1 ml/min, at 60° C. The gradient conditions used are: 90% A (0.5 g/l ammonium acetate solution), 5% B (acetonitrile), 5% C (methanol) to 50% B and 50% C in 6.5 minutes, to 100% B at 7 minutes and equilibrated to initial conditions at 7.5 minutes until 9.0 minutes. Injection volume 2 μl. High-resolution mass spectra (Time of Flight, TOF) were acquired only in positive ionization mode by scanning from 100 to 750 in 0.5 seconds using a dwell time of 0.1 seconds. The capillary needle voltage was 2.5 kV and the cone voltage was 20 V. Leucine-Enkephaline was the standard substance used for the lock mass calibration.

Method 2

In addition to the general procedure A: Reversed phase HPLC was carried out on a XDB-C18 cartridge (1.8 μm, 2.1×30 mm) from Agilent, with a flow rate of 0.8 ml/min, at 60° C. The gradient conditions used are: 90% A (0.5 g/l ammonium acetate solution), 10% B (mixture of Acetonitrile/Methanol, 1/1), to 100% B in 6.0 minutes, kept till 6.5 minutes and equilibrated to initial conditions at 7.0 minutes until 9.0 minutes. Injection volume 2 μl. Low-resolution mass spectra (SQD detector; quadrupole) were acquired only in positive ionization mode by scanning from 100 to 1000 in 0.1 seconds using an inter-channel delay of 0.08 second. The capillary needle voltage was 3 kV and the cone voltage was 20 V.

Method 3

In addition to the general procedure A: Reversed phase HPLC was carried out on a XDB-C18 cartridge (1.8 μm, 2.1×30 mm) from Agilent, with a flow rate of 0.8 ml/min, at 60° C. The gradient conditions used are: 90% A (0.5 g/l ammonium acetate solution), 10% B (mixture of Acetonitrile/Methanol, 1/1), to 100% B in 6.0 minutes, kept till 6.5 minutes and equilibrated to initial conditions at 7.0 minutes until 9.0 minutes. Injection volume 2 μl. Low-resolution mass spectra (SQD detector; quadrupole) were acquired in positive ionization mode by scanning from 100 to 1000 in 0.1 seconds using an inter-channel delay of 0.08 second. The capillary needle voltage was 3 kV. The cone voltage was 20 V and 50V for positive ionization mode and 30V for negative ionization mode.

Method 4

In addition to the general procedure B: Reversed phase HPLC was carried out on a Sunfire-C18 column (2.5 μm, 2.1×30 mm) from Waters, with a flow rate of 1.0 ml/min, at 60° C. The gradient conditions used are: 90% A (0.5 g/l ammonium acetate solution), 10% B (mixture of acetonitrile/methanol, 1/1), kept 0.20 minutes, to 100% B in 3.5 minutes, kept till 3.65 minutes and equilibrated to initial conditions at 3.8 minutes until 5.0 minutes. Injection volume 2 μl. Low-resolution mass spectra (Quadrupole, MSD) were acquired in electrospray mode by scanning from 100 to 1000 in 0.99 seconds, step size of 0.30 and peak width of 0.10 minutes. The capillary needle voltage was 1.0 kV and the fragmentor voltage was 70V for both positive and negative ionization modes.

Method 5

In addition to the general procedure A: Reversed phase HPLC was carried out on an XDB-C18 cartridge (1.8 μm, 2.1×30 mm) from Agilent, with a flow rate of 1 ml/min, at 60° C. The gradient conditions used are: 90% A (0.5 g/l ammonium acetate solution), 5% B (acetonitrile), 5% C (methanol), to 50% B, 50% C in 5.20 minutes, kept till 5.6 minutes and equilibrated to initial conditions at 5.8 minutes until 7.0 minutes. Injection volume 2 μl. High-resolution mass spectra (Time of Flight, TOF) were acquired by scanning from 100 to 750 in 0.5 seconds using a dwell time of 0.3 seconds. The capillary needle voltage was 2.5 kV for positive ionization mode and 2.9 kV for negative ionization mode. The cone voltage was 20 V for both positive and negative ionization modes. Leucine-Enkephaline was the standard substance used for the lock mass calibration.

Method 6

In addition to the general procedure A: Reversed phase HPLC was carried out on a Sunfire-C18 column (2.5 μm, 2.1×30 mm) from Waters, with a flow rate of 1.0 ml/min, at 60° C. The gradient conditions used are: 95% A (0.5 g/l ammonium acetate solution+5% of acetonitrile), 2.5% B (acetonitrile), 2.5% C (methanol) to 50% B, 50% C in 6.5 minutes, kept till 7.0 minutes and equilibrated to initial conditions at 7.3 minutes until 9.0 minutes. Injection volume 2 μl. High-resolution mass spectra (Time of Flight, TOF) were acquired by scanning from 100 to 750 in 0.5 seconds using a dwell time of 0.3 seconds. The capillary needle voltage was 2.5 kV for positive ionization mode and 2.9 kV for negative ionization mode. The cone voltage was 20 V for both positive and negative ionization modes. Leucine-Enkephaline was the standard substance used for the lock mass calibration.

Method 7

In addition to the general procedure A: Reversed phase HPLC was carried out on a BEH-C18 column (1.7 μm, 2.1×50 mm) from Waters, with a flow rate of 0.8 ml/min, at 60° C. without split to the MS detector. The gradient conditions used are: 95% A (0.5 g/l ammonium acetate solution+5% acetonitrile), 5% B (mixture of acetonitrile/methanol, 1/1), kept 0.2 minutes, to 20% A, 80% B in 3.5 minutes, to 100% B in 3.8 minutes, kept till 4.15 minutes and equilibrated to initial conditions at 4.3 minutes until 5.0 minutes. Injection volume 0.5 μl. Low-resolution mass spectra (SQD detector; quadrupole) were acquired by scanning from 100 to 1000 in 0.1 seconds using an inter-channel delay of 0.08 second. The capillary needle voltage was 3 kV. The cone voltage was 20 V for positive ionization mode and 30 V for negative ionization mode.

Method 8

In addition to the general procedure A: Reversed phase HPLC was carried out on a XDB-C18 cartridge (1.8 μm, 2.1×30 mm) from Agilent, with a flow rate of 0.8 ml/min, at 60° C. The gradient conditions used are: 90% A (0.5 g/l ammonium acetate solution), 10% B (mixture of acetonitrile/methanol, 1/1), kept 0.2 minutes, to 100% B in 3.0 minutes, kept till 3.15 minutes and equilibrated to initial conditions at 3.3 minutes until 5.0 minutes. Injection volume 2 μl. Low-resolution mass spectra (Quadrupole, SQD) were acquired by scanning from 100 to 1000 in 0.1 second using an inter-channel delay of 0.08 second. The capillary needle voltage was 3 kV. The cone voltage was 20 V and 50 V for positive ionization mode and 30 V for negative ionization mode.

Method 9

In addition to the general procedure B: Reversed phase HPLC was carried out on a XBridge-C18 column (2.5 μm, 2.1×30 mm) from Waters, with a flow rate of 1.0 ml/min, at 60° C. The gradient conditions used are: 95% A (0.5 g/l ammonium acetate solution+5% acetonitrile), 5% B (mixture of acetonitrile/methanol, 1/1), kept 0.2 minutes, to 100% B in 3.0 minutes, kept till 3.15 minutes and equilibrated to initial conditions at 3.3 minutes until 5.0 minutes. Injection volume 2 μl. Low-resolution mass spectra (Quadrupole, MSD) were acquired in electrospray mode by scanning from 100 to 1000 in 0.99 seconds, step size of 0.30 and peak width of 0.10 minutes. The capillary needle voltage was 1.0 kV and the fragmentor voltage was 70V for both positive and negative ionization modes.

Method 10

In addition to the general procedure A: Reversed phase HPLC was carried out on a BEH-C18 column (1.7 μm, 2.1×50 mm) from Waters, with a flow rate of 0.8 ml/min, at 60° C. without split to the MS detector. The gradient conditions used are: 95% A (0.5 g/l ammonium acetate solution+5% acetonitrile), 5% B (mixture of acetonitrile/methanol, 1/1), to 20% A, 80% B in 4.9 minutes, to 100% B in 5.3 minutes, kept till 5.8 minutes and equilibrated to initial conditions at 6.0 minutes until 7.0 minutes. Injection volume 0.5 μl. Low-resolution mass spectra (SQD detector; quadrupole) were acquired by scanning from 100 to 1000 in 0.1 seconds using an inter-channel delay of 0.08 second. The capillary needle voltage was 3 kV. The cone voltage was 20 V for positive ionization mode and 30 V for negative ionization mode.

Table 1: Analytical data—$R_t$ means retention time (in minutes), $[M+H]^+$ means the protonated mass of the free base of the compound, method refers to the method used for LCMS.

| Comp. Nr. | $R_t$ | $[M + H]^+$ | Method | Melting Points | Salt Form |
|---|---|---|---|---|---|
| A1 | 3.84 | n.i. | 1 | n.d. | |
| A2 | 5.38 | n.i | 1 | 127.6 | |
| A3 | 5.62 | n.i. | 2 | 156.0 | |
| A4 | 5.84 | 442 | 2 | n.d. | |
| A5 | 5.39 | 433 | 3 | 211.7 | |
| A6 | 5.71 | 438 | 3 | 156.2 | |
| A7 | 3.14 | 298 | 4 | n.d. | |
| A8 | 3.37 | 340 | 4 | n.d. | |
| A9 | 3.67 | 466 | 4 | syrup | |
| A10 | 3.59 | 408 | 5 | syrup | |
| A11 | 1.92 | 289 | 4 | n.d. | |
| A12 | 2.38 | $322^a$ | 4 | oil | |
| A13 | 3.54 | n.i. | 4 | n.d. | |
| A14 | 3.77 | n.i. | 4 | 116.7° C. | |
| A15 | 3.89 | 438 | 4 | syrup | |
| A16 | 3.90 | n.i. | 4 | syrup | |
| A17 | 2.45 | 324 | 6 | Decomposition | •HBr |
| A18 | 3.47 | 424 | 4 | 212.9° C. | |
| A19 | 3.87 | 556 | 7 | n.d. | |
| A20 | 3.55 | 433 | 8 | syrup | |
| A21 | 4.22 | 422 | 9 | syrup | |
| B1 | 3.59 | 326 | 1 | 80.6° C. | |
| B2 | 3.74 | 333 | 1 | 255.3° C. | •$CF_3CO_2H$ |
| B3 | 3.83 | 338 | 1 | Decomposition | •HCl |
| B4 | 3.03 | 308 | 1 | n.d. | •$CF_3CO_2H$ |
| B5 | 3.65 | 338 | 1 | 184.8° C. | •$CF_3CO_2H$ |
| B6 | 3.86 | 333 | 1 | 227.7° C. | •$CF_3CO_2H$ |
| B7 | 3.87 | 356 | 3 | 202° C. | •$CF_3CO_2H$ |
| B8 | 2.56 | 322 | 10 | Decomposition | •HCl | n.i.: no ionization observed.
n.d.: not determined.
$^a[M - H]^-$

Pharmacology

In vitro Binding Affinity for Human $D2_L$ Receptor

Frozen membranes of human Dopamine $D2_L$ receptor-transfected CHO cells were thawed, briefly homogenised using an Ultra-Turrax T25 homogeniser and diluted in Tris-HCl assay buffer containing NaCl, $CaCl_2$, $MgCl_2$, KCl (50, 120, 2, 1, and 5 mM respectively, adjusted to pH 7.7 with HCl) to an appropriate protein concentration optimised for specific and non-specific binding. Radioligand [$^3$H]Spiperone (NEN, specific activity ~70 Ci/mmol) was diluted in assay buffer at a concentration of 2 nmol/L. Prepared radioligand (50 μl), along with 50 μl of either the 10% DMSO control, Butaclamol ($10^{-6}$ mol/l final concentration), or compound of interest, was then incubated (30 min, 37° C.) with 400 μl of the prepared membrane solution. Membrane-bound activity was filtered through a Packard Filtermate harvester onto GF/B Unifilterplates and washed with ice-cold Tris-HCl buffer (50 mM; pH 7.7; 6×0.5 ml). Filters were allowed to dry before adding scintillation fluid and counting in a Topcount scintillation counter. Percentage specific bound and competition binding curves were calculated using S-Plus software (Insightful). Most compounds had a $pIC_{50}$ value >5.0.

Fast Dissociation

Compounds showing an $IC_{50}$ less than 10 μM were tested in an indirect assay adapted from a method published by Josee E. Leysen and Walter Gommeren, Journal of Receptor Research, 1984, 4(7), 817-845, to evaluate their rate of dissociation. Compounds at a concentration of 4 times their $IC_{50}$ were first incubated for one hour with human D2L receptor cell membranes in a volume of 2 ml at 25° C., then filtered over glass-fibre filter under suction using a 40 well multividor. Immediately after, the vacuum was released. 0.4 ml of pre-warmed buffer (25° C.) containing 1 nM [$^3$H]spiperone was added on the filter for 5 minutes. The incubation was stopped by initiating the vacuum and immediate rinsing with 2×5 ml of ice-cold buffer. The filter-bound radioactivity was measured in a liquid scintillation spectrometer. The principle of the assay is based on the assumption that the faster a compound dissociates from the D2 receptor, the faster [³H] spiperone binds to the D2 receptor. For example, when D2 receptors are incubated with clozapine at the concentration of 1850 nM (4×IC$_{50}$), [³H]spiperone binding is equivalent to 60-70% of its total binding capacity (measured in absence of drug) after 5 min incubation on filter. When incubated with other antipsychotics, [³H]spiperone binding varies between 20 and 50%. Since clozapine was included in each filtration run, tested compounds were considered fast dissociating D2 antagonists if they were dissociating as fast or faster than clozapine. Most tested compounds had a dissociation rate faster than that of clozapine, i.e. >50%.

In vitro Binding Affinity for Human D3 Receptor

Frozen membranes of human Dopamine D3 receptor-transfected CHO cells were thawed, briefly homogenized using an Ultra-Turrax T25 homogeniser and diluted in 50 mM Tris-HCl assay buffer containing 120 mM NaCl, 2 mM CaCl$_2$, 1 mM MgCl$_2$, 5 mM KCl and 0.1% BSA (adjusted to pH 7.4 with HCl) to an appropriate protein concentration optimized for specific and non-specific binding. Radioligand [¹²⁵I]Iodosulpride (Amersham, specific activity ~2000 Ci/mmol) was diluted in assay buffer at a concentration of 2 nM. Prepared radioligand (20 µl), along with 40 µl of either the 10% DMSO control, Risperidone (10⁻⁶M final concentration), or compound of interest, was then incubated with 70 µl of the prepared membrane solution and 70 µl of WGA coated PVT beads (0.25 mg/well final concentration). After shaking for 24 hours at RT plates were counted in a Topcount™ scintillation counter. Percentage specific binding and competition binding curves were calculated using S-Plus software (Insightful).

In vitro Binding Affinity for Human 5HT6 Receptor

Frozen membranes of human Serotonin 5HT6 receptor-transfected HEK cells were thawed, briefly homogenized using an Ultra-Turrax T25 homogeniser and diluted in 50 mM Tris-HCl assay buffer containing 10 mM MgCl$_2$, 1 mM EDTA and 10 µM Pargyline (adjusted to pH 7.4 with HCl) to an appropriate protein concentration optimized for specific and non-specific binding. Radioligand [³H]Lysergic acid diethylamide (Perkin Elmer, specific activity ~80 Ci/mmol) was diluted in assay buffer at a concentration of 20 nM. Radioligand (20 µl), along with 40 µl of either the 10% DMSO control, Methiothepine (10⁻⁵M final concentration), or compound of interest, was then incubated with 70 µl of the prepared membrane solution and 70 µl of WGA coated PVT beads (0.25 mg/well final concentration). After shaking for 24 hours at RT plates were counted in a Topcount™ scintillation counter. Percentage specific binding and competition binding curves were calculated using S-Plus software (Insightful).

| Ex. | D2$_L$ binding pIC$_{50}$ | D2 dissociation | 5-HT6 binding pIC$_{50}$ | D3 binding pIC$_{50}$ |
|---|---|---|---|---|
| A16 | 5.10 | 83% | 6.65 | 5.68 |
| B1 | 5.41 | n.d. | 6.91 | n.d. |
| B2 | 6.89 | 60% | 8.09 | 7.97 |
| B3 | 6.64 | 45% | 7.73 | 7.33 |
| B4 | 6.32 | 69% | 6.86 | 7.47 |
| B5 | 6.69 | 66% | 7.03 | n.d. |
| B6 | 6.33 | n.d. | 6.89 | n.d. |
| B7 | 5.47 | 89% | 6.51 | 6.43 |
| B8 | 5.32 | 95% | 6.77 | 5.68 | n.d.: not determined

The invention claimed is:

1. A compound of formula (I)

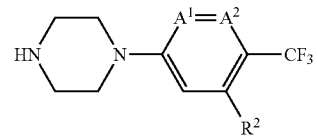

or a stereoisomeric form thereof, wherein
-A¹=A²- is —N=CR¹— or —CR¹=N—;
R¹ is hydrogen, hydroxy, halo, cyano, C$_{1-3}$alkyloxy or C$_{1-3}$alkyl;
R² is phenyl; phenyl substituted with one, two or three substituents selected from the group consisting of halo, cyano, C$_{1-3}$alkyl, hydroxyC$_{1-3}$alkyl, mono- and polyhalo -C$_{1-3}$alkyl, C$_{1-3}$alkyloxy, C$_{1-3}$alkyloxyC$_{1-3}$alkyl aminocarbonyl, mono-and di(C$_{1-3}$alkyl)aminocarbonyl, amino, mono- and di(C$_{1-3}$alkyl)amino;
pyridinyl; pyridinyl substituted with one or two substituents selected from the group consisting of halo, C$_{1-3}$ alkyloxy, arylC$_{1-3}$alkyloxy, mono- and di(C$_{1-3}$alkyl) amino, and arylC$_{1-3}$alkylamino;
thienyl substituted with one or two substituents selected from the group consisting of halo and C$_{1-3}$alkyl; or a salt thereof.

2. A compound according to claim 1 wherein
-A¹=A²- is —N=CR¹—;
R¹ is hydrogen, cyano or methoxy;
R² is phenyl or phenyl substituted with halo;
or a salt thereof.

3. A compound according to claim 1 wherein
-A¹=A²- is —CR¹=N—;
R¹ is hydrogen, methyl, cyano, hydroxy or methoxy;
R² is phenyl or phenyl substituted with halo;
or a salt thereof.

4. A pharmaceutical composition comprising a therapeutically effective amount of a compound as defined in claim 1.

5. A method for the treatment of a condition selected from the group consisting of schizophrenia, schizophreniform disorder, schizoaffective disorder, brief psychotic disorder, shared psychotic disorder, psychotic disorder due to a general medical condition, substance-induced psychotic disorder, psychotic disorder not otherwise specified and psychosis associated with dementia comprising administering a therapeutically effective amount of the compound of claim 1 to a patient in need of treatment for at least one of said conditions.

* * * * *